(12) United States Patent
Satou et al.

(10) Patent No.: US 7,211,222 B2
(45) Date of Patent: May 1, 2007

(54) GAS SENSOR

(75) Inventors: Motoaki Satou, Kariya (JP); Kiyomi Kobayashi, Kuwana (JP); Masanobu Yamauchi, Kariya (JP); Namitsugu Fujii, Yokkaichi (JP)

(73) Assignee: Denso Corporation (JP)

( * ) Notice: Subject to any disclaimer, the term of this patent is extended or adjusted under 35 U.S.C. 154(b) by 631 days.

(21) Appl. No.: 10/201,302

(22) Filed: Jul. 24, 2002

(65) Prior Publication Data

US 2003/0116435 A1 Jun. 26, 2003

(30) Foreign Application Priority Data

| Jul. 31, 2001 | (JP) | ............................. 2001-232570 |
| Jun. 5, 2002 | (JP) | ............................. 2002-164782 |

(51) Int. Cl.
*B32B 5/02* (2006.01)
*B32B 27/04* (2006.01)
*B32B 27/12* (2006.01)
*G01N 7/00* (2006.01)
*G01N 21/00* (2006.01)

(52) U.S. Cl. ........................... 422/83; 422/88; 422/94; 422/95; 422/96; 422/97; 422/98; 422/101; 436/127; 436/137; 436/139; 436/143; 436/149; 436/152; 73/1.01; 73/1.02; 73/23.2; 73/23.31; 73/23.4

(58) Field of Classification Search ................... 422/83, 422/88, 94, 95, 96, 97, 98, 10; 436/127, 436/137, 139, 143, 149, 152; 73/1.01, 1.02, 73/23.2, 23.31, 23.4
See application file for complete search history.

(56) References Cited

U.S. PATENT DOCUMENTS

| 4,088,555 | A | * | 5/1978 | Kita et al. ................... 204/428 |
| 4,857,275 | A | * | 8/1989 | Furusaki et al. .............. 422/98 |
| 4,958,514 | A | * | 9/1990 | Takami et al. ............. 73/25.03 |
| 5,039,972 | A | * | 8/1991 | Kato et al. ..................... 338/34 |
| 5,139,829 | A | * | 8/1992 | Minoha et al. ............. 427/123 |
| 5,228,975 | A | * | 7/1993 | Yamada et al. ............. 204/424 |
| 5,443,711 | A | | 8/1995 | Kojima et al. |
| 5,948,226 | A | | 9/1999 | Sakawa et al. |
| 6,273,432 | B1 | * | 8/2001 | Weyl et al. ................. 277/591 |
| 6,327,891 | B1 | | 12/2001 | Noda et al. |

(Continued)

FOREIGN PATENT DOCUMENTS

JP 2-151755 6/1990

(Continued)

OTHER PUBLICATIONS

JPO Examination Report dated Aug. 22, 2006.

*Primary Examiner*—Brian Sines
(74) *Attorney, Agent, or Firm*—Nixon & Vanderhye PC

(57) ABSTRACT

A powder filler is stuffed in a filler space defined between a housing and a gas sensing element so as to airtightly seal a clearance between the housing and the gas sensing element. The powder filler contains grains whose diameter is in a range from 80 μm to 5,000 μm when measured before being stuffed into the filler space. A weight percentage of the grains having the diameter of 80 μm to 5,000 μm is equal to or larger than 80% with respect to an overall weight of the powder filler.

31 Claims, 7 Drawing Sheets

U.S. PATENT DOCUMENTS

| | | |
|---|---|---|
| 6,347,543 B1 | 2/2002 | Geier et al. |
| 6,510,728 B2 * | 1/2003 | Matsuo et al. ............. 73/31.05 |
| 6,618,927 B2 * | 9/2003 | Tajima et al. ................. 29/595 |

FOREIGN PATENT DOCUMENTS

| | | |
|---|---|---|
| JP | 3-246458 | 11/1991 |
| JP | 8-201333 | 8/1996 |
| JP | 10-10082 | 1/1998 |
| JP | 11-248673 | 9/1999 |
| JP | 2000-146901 | 5/2000 |
| JP | 2000-314715 | 11/2000 |
| JP | 2001-124724 | 5/2001 |
| JP | 2001-281209 | 10/2001 |

* cited by examiner

GAS SENSOR

BACKGROUND OF THE INVENTION

The present invention relates to a gas sensor installed in an exhaust system of an internal combustion engine to control the combustion of this engine.

A conventional gas sensor used for controlling the combustion of an internal combustion comprises a cylindrical housing, a gas sensing element disposed in this housing, an atmospheric side cover provided at a proximal end of the housing, and a measured gas side cover provided at a distal end of the housing.

A front end (i.e., distal end) of the gas sensing element is accommodated in the measured gas side cover and is exposed to the measured gas. A proximal end of the gas sensing element is closed by the atmospheric side cover. Output terminals of the gas sensing element extend out of the gas sensor from the proximal end side.

A sealing member, an insulator, a packing or the like are provided in an annular clearance between the gas sensing element and the housing to airtightly close the clearance.

In other words, the sealing members provided between the gas sensing element and the housing serve as a partition for separating an air atmosphere in the atmospheric side cover from a measured gas atmosphere in the measured gas side cover. If the measured gas leaks into the air atmosphere from the measured gas atmosphere, the measuring accuracy of gas concentration will deteriorate. It is thus desirable to maintain high airtightness between the gas sensing element and the housing.

However, the measured gas may contain gasoline or other liquefied component. Due to its liquid nature, the gasoline or other liquefied component has the capability of smoothly penetrating into the sealing members (more specifically, micro holes and clearances residing in these sealing members). Thus, the gasoline (in the form of liquid or gas) possibly leaks into the air atmosphere. Such leakage of gasoline or other liquefied component deteriorates the accuracy in the measurement of gas concentration, too.

SUMMARY OF THE INVENTION

In view of the above-described problems, the present invention has an object to provide a gas sensor which has excellent sealing properties for preventing gasoline or other liquefied component contained in the measured gas from leaking into air atmosphere beyond the sealing members.

As a result of research and development, the inventors have found a goal to be attained and the present invention has been derived to attain this goal.

More specifically, when a powder filler contains a great amount of fine grains excluded from the later-described specific range, there is the possibility that a relatively large amount of air resides in the clearances among the grains even after the powder filler is stuffed into a filler space under a pressing force applied on the powder filler. The specific gravity of the powder filler cannot be increased so much.

On the other hand, when a powder filler contains a great amount of coarse grains excluded from the later-described specific range, there is the possibility that the coarse grains collapse insufficiently and accordingly the applied pressing force is not uniformly applied to every grains in the powder filler. Thus, the specific gravity of the powder filler cannot be increased locally. This will require an increased pressing force applied to the powder filler. The gas sensing element may break.

In order to accomplish the above and other related objects, the present invention provides a first gas sensor comprising a housing, a gas sensing element disposed in the housing, and a powder filler stuffed in a filler space defined between the housing and the gas sensing element so as to airtightly seal a clearance between the housing and the gas sensing element. The powder filler of the first gas sensor contains grains whose diameter is in a range from 80 µm to 5,000 µm when measured before being stuffed into the filler space, and a weight percentage of the grains having the diameter of 80 µm to 5,000 µm is equal to or larger than 80% with respect to an overall weight of the powder filler.

The first gas sensor of the present invention has the filler space defined between the housing and the gas sensing element. The filler space is filled with the powder filler containing relatively large grains whose size is in the above-described specific range.

The powder filler chiefly consisting of relatively large-diameter grains does not contain the residual air so much inside thereof. The specific gravity of this powder filler can be easily increased by simply adding a pressing force on this powder filler when stuffed into the filler space. Thus, after having being stuffed into the filler space, the powder filler has a high density and a higher specific gravity and accordingly the powder filler assures higher sealing properties.

Furthermore, the powder filler of the first gas sensor does not contain extremely large grains. It is not necessary to add a very large pressing force on the powder filler when the powder filler is stuffed.

In general, the volume of clearances among the grains of powder filler reduces with increasing density of the powder filler as well as with increasing specific gravity. The highly dense powder filler effectively suppresses liquid immersion caused by the capillary action.

The present invention provides a second gas sensor comprising a housing, a gas sensing element disposed in the housing, and a powder filler stuffed in a filler space defined between the housing and the gas sensing element so as to airtightly seal a clearance between the housing and the gas sensing element. The powder filler of the second gas sensor contains grains which are subjected to a classification to remove fine grains before the powder filler is stuffed into the filler space.

The powder filler of the second gas sensor is characterized in that the fine grains having extremely small diameters are removed beforehand through the classification.

In general, the powder filler deforms or collapses in the process of stuffing the powder filler into the filler space, while leaving clearances among the grains. When the powder filler is molded by a relatively large grains, the clearances are not arranged straight or sequentially so as to form an immersion path extending across the powder filler from the measured gas atmosphere to the air atmosphere. This is effective to prevent the gasoline or other liquid contained in the measured gas from leaking into the air atmosphere. Even if the clearances are connected in series so as to form a labyrinth, the overall length of the path will be long enough to suppress the gasoline or other liquid from leaking into the air atmosphere.

However, if the powder filler contains the fine grains having extremely small diameters, the fine grains will spread along the contact surfaces of the large grains. This possibly worsens the contact or bonding between the grains and possibly forms the immersion path for easily allowing the gasoline to other liquid to penetrate the powder filler.

Furthermore, there is the possibility that the fine grains concentrate locally. In this case, the fine grains will form an undesirable shortcut which party breaks the labyrinth and reduces the substantial length of this labyrinth. The capability of preventing the liquid immersion will be worsened.

Accordingly, the second gas sensor uses the powder filler containing the grains subjected to the classification to remove undesirable fine grains, thereby effectively preventing the gasoline or other liquid immersion into the air atmosphere. As a result, the second gas sensor of the present invention assures excellent sealing properties.

The present invention provides a third gas sensor comprising a housing, a gas sensing element disposed in the housing, and a powder filler stuffed in a filler space defined between the housing and the gas sensing element so as to airtightly seal a clearance between the housing and the gas sensing element. The powder filler of the third gas sensor contains grains which are subjected to a classification to remove coarse grains before the powder filler is stuffed into the filler space.

The powder filler of the third gas sensor is characterized in that the coarse grains having extremely large diameters are removed beforehand through the classification.

The powder filler deforms or collapses in the process of stuffing the powder filler into the filler space under a pressing force applied on the powder filler. The extremely coarse grains do not collapse so easily. The pressing force is not uniformly applied to every grains stuffed into the filler space. This will locally form a portion having a very small specific gravity which possibly grows or develops into an immersion path allowing the gasoline or other liquid to penetrate the powder filler.

Furthermore, when the powder filler contains the extremely coarse grains, a large pressing force is required to stuff the powder filler into the filler space. This will damage the gas sensing element or other sensor components.

From the foregoing, the third gas sensor assures excellent sealing properties.

The present invention provides a fourth gas sensor comprising a housing, a gas sensing element disposed in the housing, and a powder filler stuffed in a filler space defined between the housing and the gas sensing element so as to airtightly seal a clearance between the housing and the gas sensing element. The powder filler of the fourth gas sensor contains a supplementary filler agent.

According to the fourth gas sensor of the present invention, the supplementary filler agent is added to the powder filler.

The supplementary filler agent substantially buries or fills (i.e., eliminates) the clearances among the grains of powder filler or the contact surfaces of the grains. This increases the density of the filler and improves the bondability of the grains, and accordingly enhances the sealing properties of a gas sensor.

Furthermore, substantially eliminating the clearances among the grains of a powder filler by adding the supplementary filler agent is effective to suppresses liquid immersion caused by the capillary action.

The present invention provides a fifth gas sensor comprising a housing, a gas sensing element disposed in the housing, and a powder filler stuffed in a filler space defined between the housing and the gas sensing element so as to airtightly seal a clearance between the housing and the gas sensing element. At least one of an uneven surficial layer and an electrode protecting layer is provided on a surface of the gas sensing element. And, a proximal end of the at least one of the uneven surficial layer and the electrode protecting layer is equal to a proximal end of the filler space or offset toward a distal end side of the gas sensor with respect to the proximal end of the filler space.

According to the fifth gas sensor of the present invention, the uneven surficial layer or the electrode protecting layer is provided on the surface of the gas sensing element. These layers form a rough surface structure on the surface of the gas sensing element. There is the possibility that a labyrinth is formed along the uneven surface or in the surficial layer itself when the powder filler is stuffed into the filler space. Leaving the labyrinth is undesirable in that the liquid immersion caused by the capillary action cannot be suppressed effectively.

The electrode protecting layer is generally formed by a porous material so that a gas to be detected can diffuse and smoothly reach the sensing electrode. The porous layer cannot suppress the liquid immersion caused by the capillary action.

According to the fifth gas sensor of the present invention of the present invention, the proximal end of the uneven surficial layer or the electrode protecting layer is equal to the proximal end of the filler space or offset toward the distal end side of the gas sensor. Hence, the powder filler stuffed in the filler space can effectively block the immersion of liquid entering via the labyrinth.

The present invention provides a sixth gas sensor comprising a housing, a gas sensing element disposed in the housing, and a powder filler stuffed in a filler space defined between the housing and the gas sensing element so as to airtightly seal a clearance between the housing and the gas sensing element. The powder filler of the sixth gas sensor contains grains which are subjected to a classification to remove both of fine and coarse grains before the powder filler is stuffed into the filler space.

According to the sixth gas sensor, the extremely fine and coarse gains are removed beforehand from the powder filler. Thus, the pressing force can be uniformly applied on the powder filler when stuffed into the filler space. The powder grains uniformly collapse and bury or fill the clearances among the grains.

Furthermore, even if a labyrinth is formed in the powder filler, the overall length of this labyrinth is sufficiently long for preventing the gasoline or other liquid immersion into air atmosphere.

The required pressing force can be suppressed to a relatively lower level. The gas sensing element or other sensor component will not be damaged.

Thus, the sixth gas sensor assures excellent sealing properties.

The present invention provides a seventh gas sensor comprising a housing, a gas sensing element disposed in the housing, and a powder filler containing a supplementary filler agent stuffed in a filler space defined between the housing and the gas sensing element so as to airtightly seal a clearance between the housing and the gas sensing element. The powder filler of the seventh gas sensor contains grains whose diameter is in a range from 80 µm to 5,000 µm when measured before being stuffed into the filler space, and a weight percentage of the grains having the diameter of 80 µm to 5,000 µm is equal to or larger than 80% with respect to an overall weight of the powder filler.

The present invention provides an eighth gas sensor comprising a housing, a gas sensing element disposed in the housing, and a powder filler stuffed in a filler space defined between the housing and the gas sensing element so as to airtightly seal a clearance between the housing and the gas sensing element. The powder filler of the eighth gas sensor contains grains whose diameter is in a range from 80 µm to 5,000 µm when measured before being stuffed into the filler space, and a weight percentage of the grains having the diameter of 80 µm to 5,000 µm is equal to or larger than 80% with respect to an overall weight of the powder filler. At least one of an uneven surficial layer and an electrode protecting layer is provided on a surface of the gas sensing element. And, a proximal end of the at least one of the uneven surficial layer and the electrode protecting layer is equal to a proximal end of the filler space or offset toward a distal end side of the gas sensor with respect to the proximal end of the filler space.

The present invention provides a ninth gas sensor comprising a housing, a gas sensing element disposed in the housing, and a powder filler containing a supplementary filler agent stuffed in a filler space defined between the housing and the gas sensing element so as to airtightly seal a clearance between the housing and the gas sensing element. At least one of an uneven surficial layer and an electrode protecting layer is provided on a surface of the gas sensing element. And, a proximal end of the at least one of the uneven surficial layer and the electrode protecting layer is equal to a proximal end of the filler space or offset toward a distal end side of the gas sensor with respect to the proximal end of the filler space.

The present invention provides a tenth gas sensor comprising a housing, a gas sensing element disposed in the housing, and a powder filler containing a supplementary filler agent stuffed in a filler space defined between the housing and the gas sensing element so as to airtightly seal a clearance between the housing and the gas sensing element. The powder filler contains grains whose diameter is in a range from 80 µm to 5,000 µm when measured before being stuffed into the filler space, and a weight percentage of the grains having the diameter of 80 µm to 5,000 µm is equal to or larger than 80% with respect to an overall weight of the powder filler. At least one of an uneven surficial layer and an electrode protecting layer is provided on a surface of the gas sensing element, and a proximal end of the at least one of the uneven surficial layer and the electrode protecting layer is equal to a proximal end of the filler space or offset toward a distal end side of the gas sensor with respect to the proximal end of the filler space.

The present invention provides an eleventh gas sensor comprising a housing, a gas sensing element disposed in the housing, and a powder filler stuffed in a filler space defined between the housing and the gas sensing element so as to airtightly seal a clearance between the housing and the gas sensing element. A supplementary filler agent is added to the powder filler. The powder filler of the eleventh gas sensor contains grains which are subjected to a classification to remove both of fine and coarse grains before the powder filler is stuffed into the filler space.

The present invention provides a twelfth gas sensor comprising a housing, a gas sensing element disposed in the housing, and a powder filler stuffed in a filler space defined between the housing and the gas sensing element so as to airtightly seal a clearance between the housing and the gas sensing element. A supplementary filler agent is added to the powder filler. The powder filler contains grains which are subjected to a classification to remove both of fine and coarse grains before the powder filler is stuffed into the filler space. At least one of an uneven surficial layer and an electrode protecting layer is provided on a surface of the gas sensing element. And, a proximal end of the at least one of the uneven surficial layer and the electrode protecting layer is equal to a proximal end of the filler space or offset toward a distal end side of the gas sensor with respect to the proximal end of the filler space.

The present invention provides a thirteenth gas sensor comprising a housing, a gas sensing element disposed in the housing, and a powder filler stuffed in a filler space defined between the housing and the gas sensing element so as to airtightly seal a clearance between the housing and the gas sensing element. The powder filler of the thirteenth gas sensor contains grains which are subjected to a classification to remove both of fine and coarse grains before the powder filler is stuffed into the filler space. At least one of an uneven surficial layer and an electrode protecting layer is provided on a surface of the gas sensing element. And, a proximal end of the at least one of the uneven surficial layer and the electrode protecting layer is equal to a proximal end of the filler space or offset toward a distal end side of the gas sensor with respect to the proximal end of the filler space.

In the above-described first gas sensor of the present invention, if the weight percentage of the grains having the diameter of 80 µm to 5,000 µm is less than 80% with respect to an overall weight of the powder filler, the powder filler will contain a great amount of residual air therein due to the presence of a great amount of smaller grains. It is difficult to increase the density of the powder filler. It becomes difficult to obtain a highly dense filler.

To obtain optimized sealing properties, it is desirable that all of the grains contained in the powder filler have a grain size in the range from 80 µm to 5,000 µm.

If the powder filler contains a great amount of fine grains having the grain size less than 80 µm, the specific gravity of the powder filler will not increase so much due to a great amount of air residing therein. This will worsen the sealing properties.

In the process of stuffing the powder filler into the filler space under a pressing force applied on the powder filler, the powder grains deform or collapse in part to bury or fill the clearances among relatively coarse powder grains. If the powder filler contains a great amount of coarse grains having the grain size larger than 5,000 µm, an excessively large pressing force will be required to stuff the powder filler into the filler space. Forcibly collapsing the grains requires a large pressing force. This may damage or break the gas sensing element or other sensor components.

Regarding the method for classifying the powder grains of a powder fillers used in the second and third gas sensors, the present invention can employ the dry sieving classification, the wet sieving classification, the gravity-type dry classification utilizing airflow, the centrifugal dry classification, the rotary dry classification, the sedimentary wet classification utilizing liquid, the mechanical wet classification, and the centrifugal wet classification.

The gas sensing element of the present invention comprises a solid electrolytic body and a pair of electrodes provided on this solid electrolytic body.

One electrode is exposed to the measured gas atmosphere, and the other electrode is exposed to the air (i.e., reference gas) atmosphere.

The powder filler stuffed in the filler space is positioned at a portion separating the measured gas atmosphere and the air atmosphere respectively defined in the gas sensor.

For example, the gas sensing element of the present invention has a cup-shaped solid electrolytic body, an outside electrode provided on an outer surface of this solid electrolytic body, and an inside electrode provided on an inner surface of this solid electrolytic body.

Alternatively, the gas sensing element of the present invention can be formed into a multilayered structure consisting of solid electrolytic plates with the electrodes provided on the surfaces thereof as well as insulating plates.

In addition to the powder filler, it is desirable to employ a glass sealing material or any other sealing member to ensure airtightness between the housing and the gas sensing element.

It is needless to say that this arrangement can be applied to ant other gas sensors including multilayered gas sensors.

For example, the gas sensing element of the present invention is used for measuring the concentration of oxygen contained in the measured gas. When the gas senor is installed in an exhaust gas passage of an automotive engine, the gas sensing element of the present invention is an element capable of measuring the air-fuel ratio, or the concentration of NOx, CO, or HC contained in the exhaust gas.

According to the first gas sensor of the present invention, it is preferable that the powder filler contains the grains whose diameter is in a range from 100 µm to 1,000 µm when measured before being stuffed into the filler space and the weight percentage of the grains having the diameter of 100 µm to 1,000 µm is equal to or larger than 80% with respect to the overall weight of the powder filler.

Using the grains having the diameter of 100 µm to 1,000 µm by an amount of 80 weight % or more makes it possible to increase the specific gravity of the powder filler. Accordingly, reliable sealing properties can be obtained.

If the powder filler contains a great amount of grains having the grain size less than 100 µm, the specific gravity of the powder filler will not increase so much due to a great amount of air residing therein. This will worsen the sealing properties.

Furthermore, if the powder filler contains a great amount of grains having the grain size larger than 1,000 µm, the filling condition of grains will not be uniform. It will be difficult to give a sufficient pressing force to respective grains of the powder filler when stuffed into the filler space. This will worsen the sealing properties.

Furthermore, to obtain more excellent sealing properties, it is preferable that the powder filler of the first gas sensor contains the grains whose diameter is in a range from 125 µm to 710 µm when measured before being stuffed into the filler space and the weight percentage of the grains having the diameter of 125 µm to 710 µm is equal to or larger than 80% with respect to the overall weight of the powder filler.

Using the relatively larger powder grains is effective to reduce the residual air in the powder filler.

Furthermore, the pressing force is uniformly applied on every grains of the powder filler. The specific gravity of the molded powder filler is increased uniformly. This assures high sealing properties.

Furthermore, the pressing force required for stuffing the powder filler is relatively low.

Furthermore, it is preferable that the powder filler of the second gas sensor, after having been subjected to the classification, contains fine grains having a diameter equal to or less than 80 µm by a weight percentage equal to or less than 10% with respect to the overall weight of the powder filler.

With this arrangement, the extremely fine grains are removed adequately through the classification. It becomes possible to improve the bondability of powder grains. This eliminates a portion having a very small specific gravity which possibly grows or develops into an immersion path allowing the gasoline or other liquid to penetrate the powder filler.

Furthermore, it is preferable that the powder filler of the second gas sensor, after having been subjected to the classification, contains fine grains having a diameter equal to or less than 100 µm by a weight percentage equal to or less than 10% with respect to the overall weight of the powder filler.

With this arrangement, the extremely fine grains are further removed adequately through the classification. It becomes possible to improve the bondability of powder grains. This surely eliminates the portion having a very small specific gravity which possibly grows or develops into an immersion path allowing the gasoline or other liquid to penetrate the powder filler.

Furthermore, it is preferable that the powder filler of the second gas sensor, after having been subjected to the classification, contains fine grains having a diameter equal to or less than 125 µm by a weight percentage equal to or less than 10% with respect to the overall weight of the powder filler.

With this arrangement, the extremely fine grains are further removed adequately through the classification. It becomes possible to improve the bondability of powder grains. This surely eliminates the portion having a very small specific gravity which possibly grows or develops into an immersion path allowing the gasoline or other liquid to penetrate the powder filler.

Furthermore, it is preferable that the powder filler of the third gas sensor, after having been subjected to the classification, contains coarse grains having a diameter equal to or larger than 5,000 µm by a weight percentage equal to or less than 10% with respect to the overall weight of the powder filler.

With this arrangement, the pressing force applied on the powder filler when stuffed into the filler space can be suppressed to a lower level. No damage will be given to the gas sensing element or other sensor components. The grains having specific grain sizes deform or collapse adequately so as to form the powder filler bringing excellent sealing properties. This eliminates the immersion path allowing the gasoline or other liquid to penetrate the powder filler.

Furthermore, it is preferable that the powder filler of the third gas sensor, after having been subjected to the classification, contains coarse grains having a diameter equal to or larger than 1,000 µm by a weight percentage equal to or less than 10% with respect to the overall weight of the powder filler.

With this arrangement, it becomes possible to remove almost all of the coarse grains. The pressing force applied on the powder filler when stuffed into the filler space can be further suppressed to a lower level. No damage will be given to the gas sensing element or other sensor components. The grains having specific grain sizes surely deform or collapse adequately so as to form the powder filler bringing excellent sealing properties. This surely eliminates the immersion path allowing the gasoline or other liquid to penetrate the powder filler.

Furthermore, it is preferable that the powder filler of the third gas sensor, after having been subjected to the classification, contains coarse grains having a diameter equal to or larger than 710 µm by a weight percentage equal to or less than 10% with respect to the overall weight of the powder filler.

With this arrangement, it becomes possible to substantially remove all of the coarse grains. The pressing force applied on the powder filler when stuffed into the filler space can be further suppressed to a lower level. No damage will be given to the gas sensing element or other sensor components. The grains having specific grain sizes surely deform or collapse adequately so as to form the powder filler bringing excellent sealing properties. This surely eliminates the immersion path allowing the gasoline or other liquid to penetrate the powder filler.

According to the first to third gas sensors of the present invention, it is preferable that an axial length of the filler space is in a range from 1.5 mm to 15 mm.

This arrangement brings excellent filler properties capable of preventing immersion of liquid entering via an interface between the gas sensing element and the powder filler or an interface between the housing and the powder filler as well as liquid entering across the powder.

If the axial length of the filler space is less than 1.5 mm, the powder filler will not be able to obtain a sufficient strength. When the gas sensor is subjected to a significant thermal stress due to operation temperature change, there is the possibility that a crack may appear in the hardened filler. The produced crack will induce liquid immersion.

If the axial length of the filler space is larger than 15 mm, a large frictional force will act at an interface between the powder filler and the gas sensing element as well as at an interface between the powder filler and the housing when the powder filler is stuffed into the filler space. This will make it difficult to uniformly apply a pressing load to the powder filler. The specific gravity will disperse locally. The portion having a relatively low specific gravity may be difficult to prevent the liquid immersion.

The axial length of the filler space is defined as a vertical (i.e., axial) distance from a distal end of the filler space to a proximal end of the filler space in the axial direction of the gas sensing element.

According to the first to third gas sensors of the present invention, it is preferable that the powder filler contains at least one of talc and boron nitride by an amount of 50 weight % or more.

Using the above-identified powder filler is advantageous in that the scaly grains contained in this powder filler form a layered structure when the powder filler is stuffed into the filler space. The specific gravity of the powder filler containing scaly grains becomes higher compared with that of a powder filler containing ball grains. This is effective to eliminate the penetrating path extending across the powder filler, thereby prevent the immersion of gasoline or other liquid.

Furthermore, the scaly grains can densely fill the clearance between the powder filler and the gas sensing element as well as the clearance between the powder filler and the housing.

Especially, the talc powder is a layered compound consisting of scaly grains. When a pressing force is applied on the talc powder, the talc powder causes cleavage in the layered direction without destroying the layered construction of the scaly grains of talc. The talc powder is sufficiently soft to bury the clearances caused by the cleavage. More specifically, the scaly grains of talc corrupt and fill the filler space densely. The specific gravity can be increased so as to assure excellent sealing properties.

If the content of the at least one of talc or boron nitride is less than 50 weight %, the layered structure of scaly grains will not be formed sufficiently. This will allow the gasoline or other liquid to easily penetrate the powder filler.

According to the fourth gas sensor of the present invention, the supplementary filler agent is added to the powder filler. In this case, it is possible to add other materials.

For example, a small amount of alumina powder is added to the powder filler. The alumina powder buries or fills the clearances among the grains of powder filler.

It is also possible to add spinel, zirconia, titania and silica.

According to the fourth gas sensor of the present invention, it is preferable that the supplementary filler agent is water solution of inorganic compound which is in a liquid state at a room temperature (20° C.).

Due to its liquid nature, The water solution of inorganic compound smoothly and efficiently buries or fills the clearances among the grains of powder filler. The powder filler can be highly densified so as to obtain excellent sealing properties.

In this case, it is preferable that the liquid supplementary filler agent if the fourth gas sensor contains at least one selected from the group consisting of water solution of aluminum primary phosphate, water solution of sodium silicate, and water solution of potassium silicate.

Especially, to obtain excellent sealing properties, it is preferable that the liquid supplementary filler agent contains water solution of aluminum primary phosphate.

Furthermore, it is also preferable that an additive amount of the liquid supplementary filler agent (in a liquid state at the room temperature 20° C.) of the fourth gas sensor is in a range from 0.1 to 10 weight part with respect to 100 weight part of the powder filler.

If the additive amount of the liquid supplementary filler agent is less than 0.1 weight part, it will be difficult to completely bury or fill the clearances among the grains of the powder filler. The, denseness of powder filler will be dissatisfactory.

On the other hand, if the additive amount of the liquid supplementary filler agent is larger than 10 weight part, it will be difficult to increase the specific weight of the powder filler to a required level due to presence of a great amount of liquid. This will lead to deterioration of sealing properties.

Alternatively, it is preferable that the supplementary filler agent of the fourth gas sensor is a solid inorganic compound which is liquefiable at a temperature of 600° C. or less.

After this solid inorganic compound is stuffed into the filler space, the solid inorganic compound is liquefied by applying a heat treatment or when the gas sensor is heated up to this temperature level during its operation. The liquefied inorganic compound smoothly and efficiently buries or fills the clearances among the grains of powder filler. The powder filler can be highly densified so as to obtain excellent sealing properties.

In this case, it is preferable that the solid supplementary filler agent of the fourth gas sensor contains at least one selected from the group consisting of barium hydroxide, borosilicate glass, aluminosilicate glass, soda-lime silicate glass, lead silicate glass, low-melting borate glass, lime-alumino group glass, and aluminate glass.

The materials consisting of the above-identified group are liquefied at relatively low temperatures.

Accordingly, the heat treatment of a relatively low temperature is applied to the powder filler to liquefy the solid inorganic compound. No adverse thermal influence will be given to the housing, the gas sensing element, and other components of a gas sensor.

It is also preferable that an additive amount of the solid supplementary filler agent of the fourth gas sensor is in a range from 0.5 to 30 weight part with respect to 100 weight part of the powder filler.

When the additive amount of the solid supplementary filler agent is in the above-identified range, the powder filler can be highly densified.

If the additive amount of the solid supplementary filler agent is less than 0.5 weight part, it will be difficult to completely bury or fill the clearances among the grains of the powder filler. An immersion path will be formed in the powder filler. The gasoline or other liquid contained in the exhaust gas to be measured will penetrate into the powder filler through the immersion path thus formed.

If the additive amount of the solid supplementary filler agent is larger than 30 weight part, the denseness of the powder filler will be rather worsened due to surplus of the added supplementary filler agent.

The fifth gas sensor of the present invention has at least one of the uneven surficial layer and the electrode protecting layer formed on a surface of the gas sensing element.

The uneven surficial layer is provided on the surface of a solid electrolytic body constituting the gas sensing element. The electrode protecting layer covers an electrode formed on the surface of the solid electrolytic body.

Providing the uneven surficial layer is effective to enhance the adhesion between the electrode and the electrode protecting layer. The electrode protecting layer has a function of protecting the electrode against poisonous substances contained in the measured gas.

The electrode protecting layer is made of a porous material which allows the measured gas to penetrate or diffuse across this layer and reach the electrode.

It is possible to provide only one of the uneven surficial layer and the electrode protecting layer on the gas sensing element. It is also possible to provide both of the uneven surficial layer and the electrode protecting layer on the gas sensing element.

According to the fifth gas sensor of the present invention, it is preferable that the at least one of the uneven surficial layer and the electrode protecting layer is offset toward the distal end side of the gas sensor with respect to the proximal end of the filler space by an amount of 0.5 mm or more.

Satisfying this condition makes it possible to interrupt the immersion path at the proximal end side of the filler space. Thus, the gasoline or other liquid contained in the exhaust gas can be surely prevented from leaking into the air atmosphere beyond the powder filler via the immersion path.

If the offset amount is less than 0.5 mm, the sealing properties will deteriorate slightly.

The lower limit of the offset amount is 0 mm.

It is also preferable in the fifth gas sensor that the proximal end of the at least one of the uneven surficial layer and the electrode protecting layer is equal to a distal end of the filler space or offset toward the distal end side of the gas sensor with respect to the distal end of the filler space.

Satisfying this condition is preferable to eliminate the immersion path from the interface between the powder filler and the gas sensing element. The sealing properties of the powder filler can be increased greatly.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Figure 1:
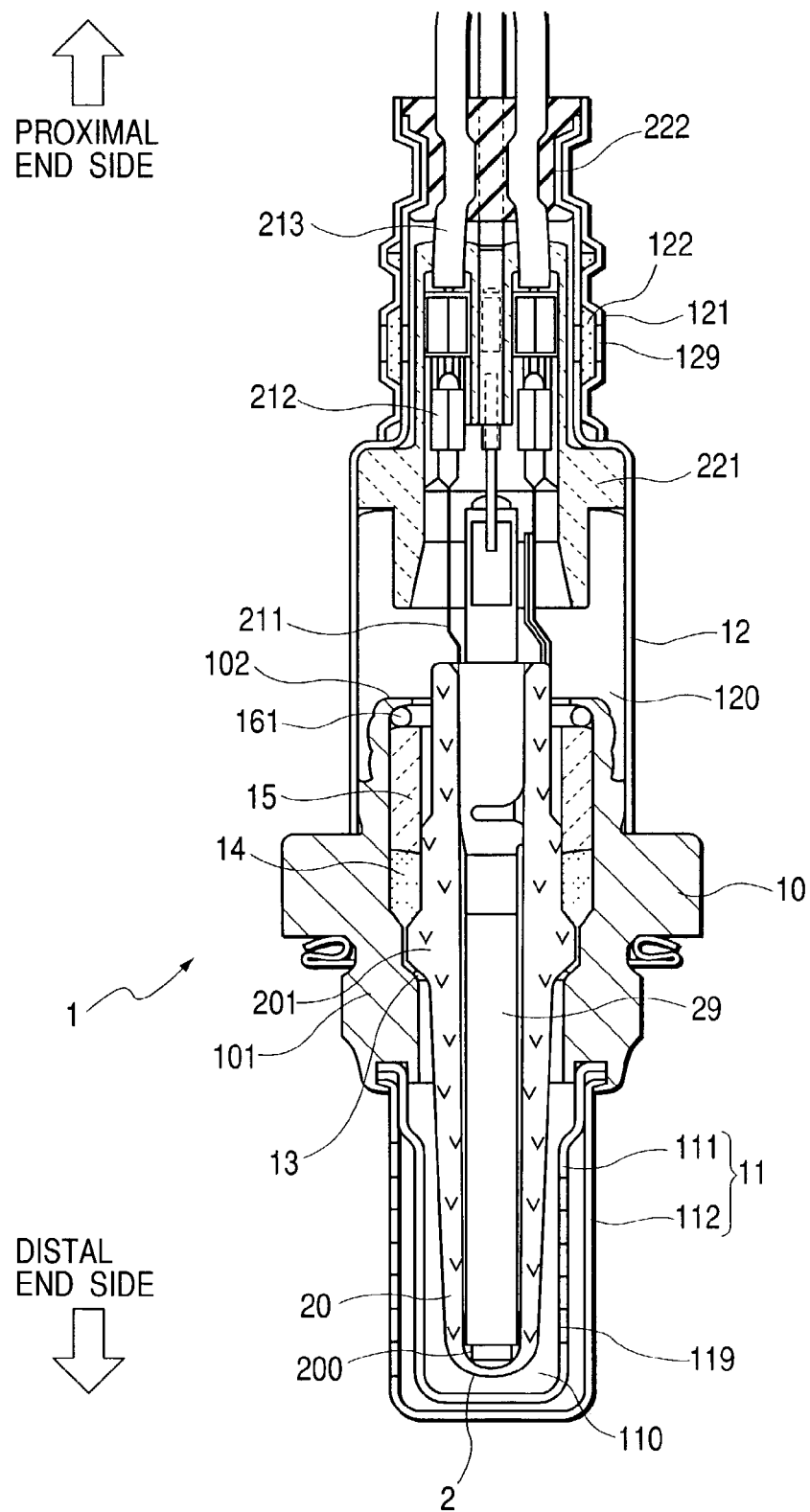
FIG. 1 is a vertical cross-sectional view showing a gas sensor in accordance with a preferred embodiment of the present invention.

Preferred embodiments of the present invention will be explained hereinafter with reference to attached drawings. Identical parts are denoted by the same reference numerals throughout the drawings.

First Embodiment

Figure 2:
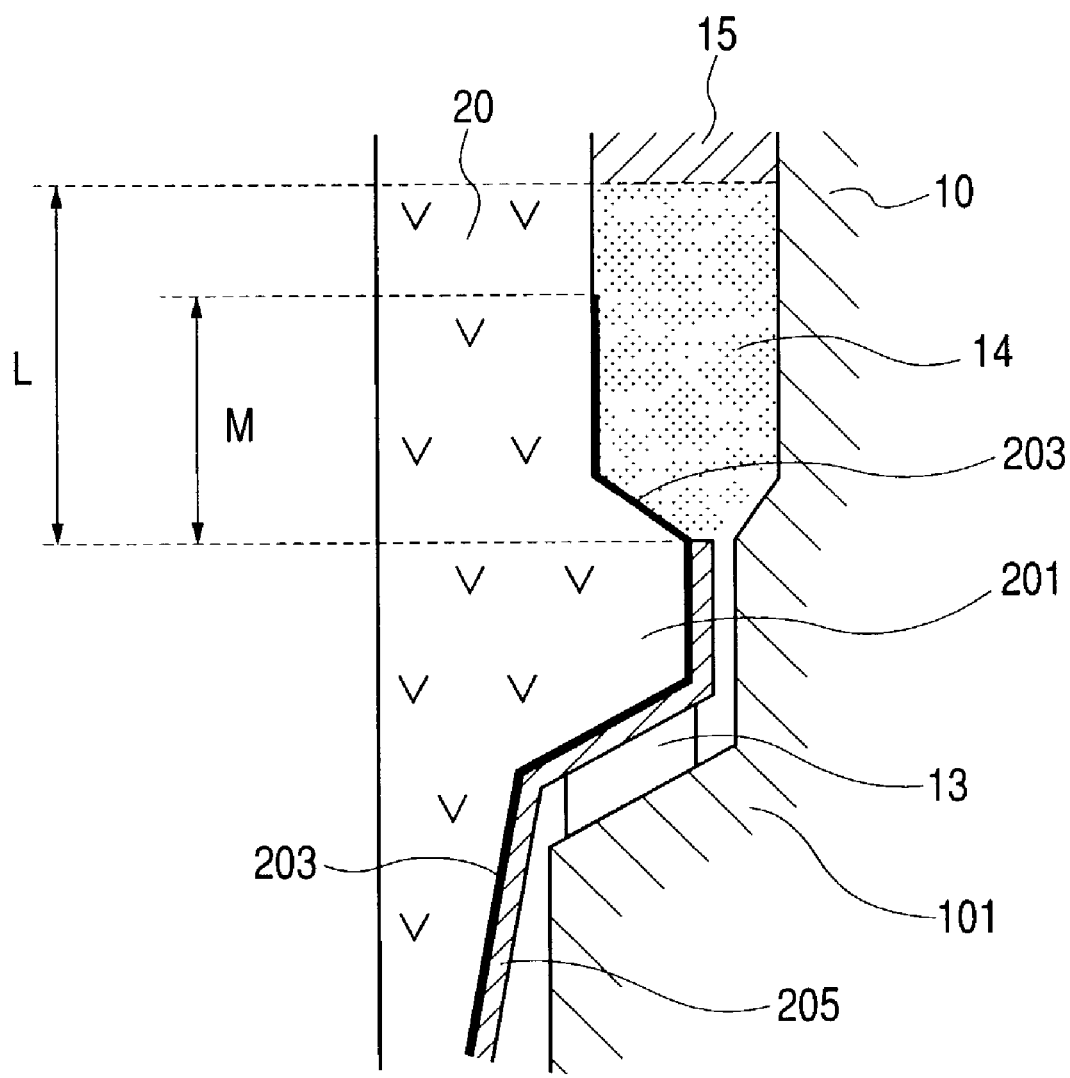
FIG. 2 is an enlarged vertical view showing an essential arrangement of the gas sensor in accordance with the preferred embodiment of the present invention.

FIGS. 1 and 2 show a gas sensor 1 in accordance with a first embodiment of the present invention. The gas sensor 1 comprises a housing 10, a gas sensing element 2 disposed in an inside space of housing 10, and a filler space 14 defined between the housing 10 and the gas sensing element 2. The filler space 14 is filled with a powder filler which airtightly seals an annular clearance between the housing 10 and the gas sensing element 2.

The powder filler contains grains whose diameter (i.e., grain size) is in the range from 80 μm to 1,000 μm when measured before being stuffed into the filler space. The weight percentage of the grains having the diameter of 80~1,000 μm is equal to or larger than 80% with respect to an overall weight of the powder filler.

The gas sensor in accordance with the first embodiment is an air-fuel ratio sensor which is installed in an exhaust gas passage of an automotive vehicle engine to control combustion of the engine.

The housing 10, shown in FIG. 1, is a metallic cylindrical housing. The gas sensing element 2 is inserted into the inside space of housing 10. A measured gas side cover 11 is attached to a distal end of housing 10. An atmospheric side cover 12 is provided at a proximal end of housing 10. In FIG. 1, the lower side of gas sensor 1 is referred to as distal end side and the upper side of gas sensor 1 is referred to as proximal end side.

The measured gas side cover 11 consists of an inside cover 111 and an outside cover 112 which cooperatively constitute a double-layered structure. Each of inside cover 111 and outside cover 112 is provided with a plurality of gas introducing holes 119. The measured gas is introduced into the measured gas side cover 11 via gas introducing holes 119 from the outside of gas sensor 1 to form a measured gas atmosphere 110.

An outside cover 121 is provided at the proximal end side of the atmospheric side cover 12. A water repellent filer 122 is interposed between the outside cover 121 and the atmospheric side cover 12. Each of the atmospheric side cover 12 and outside cover 121 is provided with a plurality of air introducing holes 129 at the portion facing the water repellent filer 122. Air is introduced into the atmospheric side cover 12 via the air introducing holes 129 to form an air atmosphere 120.

The gas sensing element 2 comprises a cup-shaped solid electrolytic body 20. Although not shown in the drawings, a pair of outside and inside electrodes are provided on an outer and inner surfaces of the solid electrolytic body 20, respectively. An atmospheric chamber 200 is provided in the solid electrolytic body 20. The atmospheric chamber 200 communicates with the air atmosphere 120.

The solid electrolytic body 20 has a uneven or irregular surficial layer 203 as shown in FIG. 2. Furthermore, a diffusion resistive layer (not shown) and an electrode protecting layer 205 are provided to cover the outside electrode (not shown) formed on the solid electrolytic body 20.

The solid electrolytic body 20 of gas sensing element 2 comprises a protruding portion 201 protruding in the radially outward direction from the outer surface thereof. The housing 10 has a receiving portion 101 protruding in the radially inward direction from the inner surface thereof. The protruding portion 201 of solid electrolytic body 20 is received by the receiving portion 101 of housing 10. A metallic packing 13 is disposed between a lower surface of protruding portion 201 and the receiving portion 101. In other words, the solid electrolytic body 20 is mounted at the lower surface of protruding portion 201 on the receiving portion 101 of housing 10 via the metallic packing 13.

The filler space 14 is defined between an upper surface of protruding portion 201 of the solid electrolytic body 20 and the inner surface of housing 10. The filler space 14 is filled with the powder filler containing supplementary filler agent. An insulator 15 is provided in the annular clearance between the outer surface of solid electrolytic body 20 and the inner surface of housing 10. The insulator 15 is disposed on the powder filler stuffed in the filler space 14.

A caulking metal ring 161 is disposed at an upper end of insulator 15. A proximal (i.e., upper) end 102 of housing 10 is caulked radially inward along the caulking metal ring 161. The insulator 15 is thus firmly fixed to by upper part of housing 10 so as to plug the powder filler stuffed in the filler space 14.

Furthermore, terminals 211 of the gas sensing element 2 extend in the atmospheric cover 12. The terminals 211 are connected to lead wires 213 via metal connectors 212. The metal connectors 212 are disposed in the atmospheric cover 12. The lead wires 213 extend out of the gas sensor 1. An atmospheric side insulator 221 is placed at an intermediate portion inside the atmospheric cover 12. An elastic insulating member 222 is placed at the proximal end inside the atmospheric cover 12. A heater 29 is placed in the atmospheric chamber 200 of the cup-shaped solid electrolytic body 20.

The above-described powder filler is talc powder. Talc is one of clay minerals which is a natural material chiefly containing $Mg_3Si_4O_{10}(OH)_2$. The talc powder used in this embodiment contains the grains having the grain size in the range from 80 μm to 1,000 μm by an amount of 80 weight % or more.

The filler space 14 of this embodiment is manufactured in the following manner.

First, the metallic packing 13 and the gas sensing element 2 are successively put into the inner space of housing 10 and are placed in position as illustrated in the drawing. Meanwhile, the powder filler of talc is molded into a ring shape beforehand.

Next, the talc powder filler is put into the annular clearance between the sensing element 2 and the housing 10.

Then, a predetermined pressing force is applied on the talc powder filler in the axial direction from the proximal end side (i.e., upper end side) of the gas sensor 1 until the talc powder filler is hardened in the filler space 14.

Then, the insulator 15 and the caulking metal ring 161 are successively put on the hardened powder filler from the proximal end side of the gas sensor 1. Then, the proximal (i.e., upper) end 102 of housing 10 is caulked radially inward along the caulking metal ring 161.

Regarding the preliminary molding operation for obtaining the ring-shaped talc powder filler, an appropriate amount of water is added to the talc powder to improve the shape retainability of the molded filler before the talc powder is put between ring-shaped dies. A press machine applies a pressing force to the talc powder via the dies so as to mold the talc powder into the ring-shape powder filler.

It is preferable if necessary to dry the moisture components contained in the powder filler after accomplishing the preliminary molding operation or after installing the molded powder filler into the housing 10.

Regarding the installation of talc powder filler into the housing 10, it is also possible to directly supply the talc powder into the housing 10 by skipping the preliminary molding operation.

As shown in FIG. 2, the uneven surficial layer 203 is formed on the solid electrolytic body 20 of gas sensing element 2. The uneven surficial layer 203 extends from the distal end of solid electrolytic body 20 to the protruding portion 201 of solid electrolytic body 20. The outside electrode (not shown) is provided so as to cover the uneven surficial layer 203.

An axial length L of filler space 14 and an axial length M of uneven surficial layer 203 are regulated in the following manner.

The axial length L of filler space 14 is defined as a vertical (i.e., axial) distance from a distal end of filler space 14 to a proximal end of filler space 14 in the axial direction of gas sensing element 2.

The axial length M of uneven surficial layer 203 is defined as a vertical (i.e., axial) distance from the proximal end (i.e., upper end) of the uneven surficial layer 203 to the distal end (i.e., lower end) of the filler space 14.

According to the embodiment shown in FIG. 2, L is 3.5 mm and M is 2.5 mm.

The gas sensor in accordance with the first embodiment has the following functions and effects.

The gas sensor 1 of this embodiment has the filler space 14 defined between the housing 10 and the gas sensing element 2. The filler space 14 is filled with the powder filler containing relatively large grains whose size is in the above-described specific range.

The powder filler chiefly consisting of large-diameter grains does not contain the air so much inside thereof. The specific gravity of the powder filler can be easily increased by simply adding a pressing force on this powder filler when stuffed into the filler space 14. Thus, after having being stuffed into the filler space 14, the powder filler has a high density and a higher specific gravity and accordingly the powder filler assures higher sealing properties.

In general, the clearances (volume) among the grains of powder filler reduces with increasing density of the powder filler as well as with increasing specific gravity. The highly dense powder filler effectively suppresses liquid immersion caused by the capillary action.

Liquid components cannot penetrate into or pass through the clearance between the housing 10 and the gas sensing element 2. The gas sensor 1 of this embodiment has excellent airtightness.

The gas sensor of this embodiment is installed in the exhaust gas passage of an automotive vehicle engine to control the combustion of this engine. The measured gas emitted from the engine contains gasoline. The gas sensor of this embodiment prevents the gasoline from leaking into the air atmosphere 120 via the filler space 14 because the highly dense powder filler is stuffed in the filler space 14.

The powder filler is made of talc. The talc powder is a layered compound consisting of scaly grains. When a pressing force is applied on the talc powder, the talc powder causes cleavage in the layered direction without destroying the layered construction of the scaly grains of talc. The talc powder is sufficiently soft to bury the clearances caused by the cleavage. More specifically, the scaly grains of talc corrupt and fill the filler space densely. The specific gravity can be increased so as to assure excellent sealing properties.

Furthermore, it is preferable to add the supplementary filler agent to the powder filler. The added supplementary filler agent smoothly enters into the clearances among the grains of powder filler and effectively buries or fills the clearances. The density of powder filler in the filler space 14 is preferably increased.

For example, the supplementary filler agent is the aluminum primary phosphate which is a liquid compound containing water of crystallization. When a pressing force is applied on the powder filler, the aluminum primary phosphate smoothly enters into the clearances among the grains of powder filler or extends along the grains of powder filler. Thus, the aluminum primary phosphate effectively buries or fills the clearances among the grains of powder filler. Accordingly, it becomes possible to increase the density of powder filler in the filler space 14.

Regarding the mixing of the talc powder and the supplementary filler agent, the mixing operation is performed in the following manner.

Each of the talc powder and the supplementary filler agent is weighed. The supplementary filler agent is added to the talc powder. An appropriate amount of water is also added to the talc powder. Then, the talc powder and the supplementary filler agent are mixed uniformly in a rotary mixer at appropriate speeds so as not to collapse the talc powder grains. Then, the talc powder is molded into a ring-shaped filler, as described above.

Alternatively, it is possible to add an appropriate amount of water to the supplementary filler agent beforehand. Then, the water-added supplementary filler agent is sprayed onto the talc powder while the talc powder is rotated in the rotary mixer. Mixing the water-added supplementary filler agent with the talc powder in this manner is effective to quickly accomplish the mixing operation of the talc powder and the supplementary filler agent without collapsing the talc powder grains.

Measurement of the sealing properties of the powder filler in accordance with the above-described embodiment was checked in the following manner.

Figure 3A:
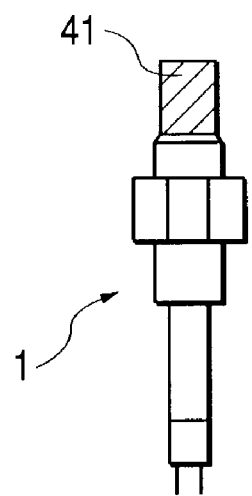
FIGS. 3A, 3B and 3C are views explaining a method for testing gasoline sealing properties.

First, as shown in FIG. 3A, the gas sensor 1 was held upright with the proximal end of gas sensor 1 being directed downward. Next, the outer surface of the measured gas side cover was concealed by a seal tape 41.

Figure 3B:
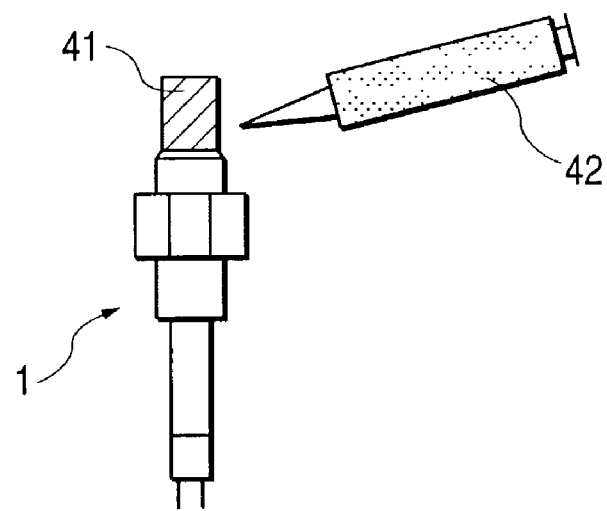
Figure 3C:
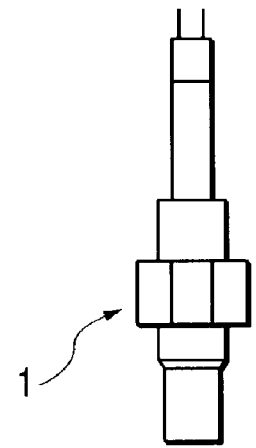

Then, as shown in FIG. 3B, a small amount (0.5 cc) of gasoline was injected into the measured gas side cover by using am appropriate injector 42. After completing the injection of gasoline, the gas sensor 1 was left for a predetermined time. Then, the seal tape 41 was removed. The remaining gasoline was discharged out of the measured gas side cover as shown in FIG. 3C.

In this condition, a voltage of 13.5 V was applied to the heater in the gas sensor 1 for two hours to monitor the change of an output of gas sensor 1.

Figure 4:
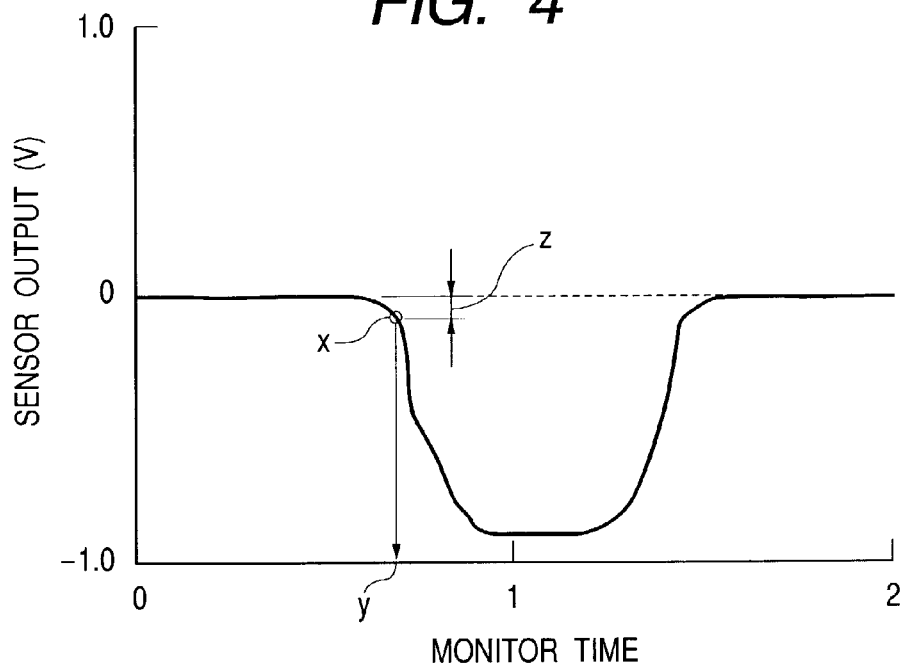
FIG. 4 is a time chart showing the relationship between sensor output and monitor time during the gasoline sealing properties test.

FIG. 4 is a time chart showing a measured output of gas sensor 1 during the two-hour monitoring.

As understood from FIG. 4, the sensor output was stationary in the beginning of the two-hour monitoring. However, after elapse of approximately one third of the two-hour monitoring ($\approx$40 minutes), the sensor output has suddenly declined. Then, the sensor output was kept in a relatively low level for a while. Then, after elapse of a significant time (i.e., at the time corresponding to approximately two thirds of the two-hour monitoring), the sensor output has resumed to the initial level.

In FIG. 4, 'x' represents a point where the sensor output is lower than the initial level by an amount of 'z', while 'y' represents a time the point 'x' was measured.

In the following evaluations of gas sensor samples, ⊚ represents a gas sensor sample having caused an output deterioration less than 0.05V, ○ represents a gas sensor sample having caused an output deterioration in a range from 0.05V to 0.1V, and × represents a gas sensor sample having caused an output deterioration larger than 0.1V.

The gas sensor samples having demonstrated small output deteriorations are recognized as possessing excellent sealing properties against gasoline at their powder fillers. On the contrary, the gas sensor samples having caused large sensor output deteriorations are recognized as possessing poor sealing properties against gasoline at their powder fillers.

A total of twenty-five samples, sample #1 to sample #25, ware prepared to evaluate the performance of the gas sensor in accordance with the above-described embodiment.

Table 1 and Table 2 show the distribution of diameters of grains contained in the powder filler of each sample. Numerals P1 to P11 attached to some powder fillers denote the type of grain size distribution.

Types P1 and P2 are too much small in grain size. On the other hand, type P10 is too much large in grain size. In other words, types P1, P2 and P3 do not satisfy the condition that the powder filler contains the grains having the diameter 80~5,000 μm by an amount of 80 weight % or more.

Type P11 has a grain size distribution spreading widely from small grain sizes to large grain sizes. Type P11 satisfies the condition that the powder filler contains the grains having the diameter 80~5,000 μm by an amount of 80 weight % or more.

The powder fillers of gas sensor samples #18 to #25 are classified into type P6. The powder fillers of gas sensor samples #1 to #23 are made of talc. The powder fillers of gas sensor samples #24 and #25 are respectively made of a mixture of talc and alumina.

Table 2 summarizes the measurement result of gas sensor samples #1 to #25 shown in Table 1.

From the result shown in Tables 1 and 2, gas sensor samples #1 and #2 are classified into types P1 and P2 having too much small grain sizes. Each of the gas sensor samples

1 and #2 has poor gasoline sealing properties at the powder filler disposed in the filling space and therefore causes a large sensor output reduction. Furthermore, gas sensor sample #16 is classified into type P10 having too much large grain sizes. The gas sensor sample #16 has bad gasoline sealing properties at the powder filler disposed in the filling space and therefore causes a large sensor output reduction.

From the foregoing, it is confirmed that excellent sealing properties can be assured for a gas sensor when the powder filler contains the grains whose size (i.e., diameter) is in the range from 80 μm to 5,000 μm when measured before being stuffed into the filler space and the weight percentage of the grains having the grain size of 80~5,000 μm is 80% or more with respect to an overall weight of the powder filler.

Furthermore, types P4 to P7 (ranging from gas sensor samples #4 to #13) are characterized in that the powder filler contains the grains whose size (i.e., diameter) is in the range from 100 μm to 1,000 μm when measured before being stuffed into the filler space and the weight percentage of the grains having the grain size of 100~1,000 μm is 80% or more with respect to an overall weight of the powder filler. The gas sensor samples classified into types P4 to P7 were evaluated as having excellent gasoline sealing properties at their powder fillers (indicated by ◎ in Table 2).

Furthermore, gas sensor samples #18 to #25 are classified into type P6. The gas sensor sample #18 is short (1 mm) in the axial length of filler space. The gas sensor sample #18 has shown a relatively large sensor output reduction, although the evaluation is not bad (○).

All of the gas sensor samples #19 to #22 have demonstrated excellent gasoline sealing properties (◎) although they are differentiated from each other in the axial length of filler space.

The powder filler of gas sensor sample #23 is made of boron nitride. The gas sensor sample #23 has demonstrated excellent gasoline sealing properties (◎). The powder fillers of gas sensor samples #24 and #25 are respectively made of a mixture of talc and alumina. The gas sensor sample #25 has shown a relatively large sensor output reduction.

From the foregoing measurement result, it is confirmed that the sensor output is somewhat influenced by the axial length of filler space as well as by the material of powder filler. The powder filler made of talc or boron nitride brings excellent gasoline sealing properties for a gas sensor.

TABLE 1

| Sample No. | Distribution (weight %) of Grains with respect to Grain Diameter (μm) | | | | | | | | | Evaluation | Type of Grain Size Distribution |
|---|---|---|---|---|---|---|---|---|---|---|---|
| | ~80 | 80~100 | 100~125 | 125~250 | 250~710 | 710~810 | 810~1000 | 1000~5000 | 5000~ | | |
| 1 | 100 | 0 | 0 | 0 | 0 | 0 | 0 | 0 | 0 | X | P1 |
| 2 | 24 | 13 | 11 | 29 | 23 | 0 | 0 | 0 | 0 | X | P2 |
| 3 | 15 | 11 | 11 | 30 | 33 | 0 | 0 | 0 | 0 | ○ | P3 |
| 4 | 3 | 7 | 17 | 30 | 43 | 0 | 0 | 0 | 0 | ◎ | P4 |
| 5 | 0 | 3 | 8 | 29 | 43 | 6 | 11 | 0 | 0 | ◎ | P5 |
| 6 | 0 | 0 | 0 | 40 | 52 | 8 | 0 | 0 | 0 | ◎ | |
| 7 | 0 | 0 | 0 | 80 | 20 | 0 | 0 | 0 | 0 | ◎ | |
| 8 | 0 | 0 | 0 | 37 | 63 | 0 | 0 | 0 | 0 | ◎ | P6 |
| 9 | 0 | 0 | 0 | 20 | 80 | 0 | 0 | 0 | 0 | ◎ | |
| 10 | 0 | 0 | 0 | 0 | 100 | 0 | 0 | 0 | 0 | ◎ | |
| 11 | 0 | 0 | 0 | 0 | 87 | 13 | 0 | 0 | 0 | ◎ | |
| 12 | 0 | 0 | 0 | 0 | 73 | 9 | 18 | 0 | 0 | ◎ | |
| 13 | 0 | 0 | 0 | 23 | 42 | 5 | 10 | 20 | 0 | ◎ | P7 |
| 14 | 0 | 0 | 0 | 12 | 40 | 5 | 13 | 30 | 0 | ○ | P8 |
| 15 | 0 | 0 | 0 | 0 | 0 | 3 | 5 | 72 | 20 | ○ | P9 |
| 16 | 0 | 0 | 0 | 0 | 0 | 0 | 3 | 67 | 30 | X | P10 |
| 17 | 17 | 2 | 11 | 22 | 37 | 4 | 7 | 0 | 0 | ○ | P11 |
| 18 | 0 | 0 | 0 | 37 | 63 | 0 | 0 | 0 | 0 | ○ | P6 |
| 19 | 0 | 0 | 0 | 37 | 63 | 0 | 0 | 0 | 0 | ◎ | P6 |
| 20 | 0 | 0 | 0 | 37 | 63 | 0 | 0 | 0 | 0 | ◎ | P6 |
| 21 | 0 | 0 | 0 | 37 | 63 | 0 | 0 | 0 | 0 | ◎ | P6 |
| 22 | 0 | 0 | 0 | 37 | 63 | 0 | 0 | 0 | 0 | ◎ | P6 |
| 23 | 0 | 0 | 0 | 37 | 63 | 0 | 0 | 0 | 0 | ◎ | |
| 24 | 0 | 0 | 0 | 37 | 63 | 0 | 0 | 0 | 0 | ○ | |
| 25 | 0 | 0 | 0 | 37 | 63 | 0 | 0 | 0 | 0 | X | |

TABLE 2

| Sample No. | Axial Length of Filler Space (mm) | Powder Filler | Evaluation | Type of Grain Size Distribution |
|---|---|---|---|---|
| 1 | 4 | talc | X | P1 |
| 2 | 4 | talc | X | P2 |
| 3 | 4 | talc | ○ | P3 |
| 4 | 4 | talc | ◎ | P4 |
| 5 | 4 | talc | ◎ | P5 |
| 6 | 4 | talc | ◎ | |
| 7 | 4 | talc | ◎ | |
| 8 | 4 | talc | ◎ | P6 |
| 9 | 4 | talc | ◎ | |
| 10 | 4 | talc | ◎ | |
| 11 | 4 | talc | ◎ | |
| 12 | 4 | talc | ◎ | |
| 13 | 4 | talc | ◎ | P7 |
| 14 | 4 | talc | ○ | P8 |
| 15 | 4 | talc | ○ | P9 |
| 16 | 4 | talc | X | P10 |
| 17 | 4 | talc | ○ | P11 |
| 18 | 1 | talc | ○ | P6 |
| 19 | 1.5 | talc | ◎ | P6 |
| 20 | 10 | talc | ◎ | P6 |

TABLE 2-continued

| Sample No. | Axial Length of Filler Space (mm) | Powder Filler | Evaluation | Type of Grain Size Distribution |
|---|---|---|---|---|
| 21 | 15 | talc | ◎ | P6 |
| 22 | 20 | talc | ◎ | P6 |
| 23 | 4 | boron nitride | ◎ | |
| 24 | 4 | talc 60 wt % + alumina 40 wt % | ○ | |
| 25 | 4 | talc 50 wt % + alumina 50 wt % | X | |

Next, the influence of removing fine grains from the powder filler was checked by evaluating several gas sensor samples in the following manner.

Table 3 shows the distribution of grains, the classification method, evaluation result, and the type of grain size distribution of respective tested gas sensor samples #99 to #105.

Due to the presence of a great amount of fine grains, gas sensor sample #99 has poor gasoline sealing properties and accordingly has caused a large sensor output deterioration.

Other gas sensor samples #100 to #105 have relatively good gasoline sealing properties (evaluated ○ or ◎). From this fact, it is confirmed that removing the fine grains is effective to obtain a powder filler having excellent gasoline sealing properties.

From the comparison between #100 and other samples #101–#105, it is understood that removing the fine grains having the grain size of 80 μm or less is very effective to enhance the gasoline sealing properties.

TABLE 3

| | Distribution (weight %) of Grains with respect to Grain Diameter (μm) | | | | | | | | | | Type of Grain Size Distri. |
|---|---|---|---|---|---|---|---|---|---|---|---|
| Sample No. | ~80 | 80~100 | 100~125 | 125~250 | 250~710 | 710~810 | 810~1000 | 1000~5000 | 5000~ | Method of classification | Evaluation | |
| 99 | 30 | 8 | 7 | 12 | 15 | 12 | 8 | 5 | 3 | Nothing | X | P12 |
| 100 | 12 | 10 | 14 | 18 | 19 | 11 | 9 | 4 | 3 | dry sieving classification (aperture 40 μm) | ○ | |
| 101 | 5 | 12 | 13 | 17 | 20 | 14 | 12 | 5 | 2 | dry sieving classification (aperture 80 μm) | ◎ | |
| 102 | 2 | 6 | 14 | 20 | 18 | 18 | 14 | 6 | 2 | dry sieving classification (aperture 100 μm) | ◎ | |
| 103 | 1 | 2 | 5 | 18 | 22 | 21 | 23 | 6 | 2 | dry sieving classification (aperture 125 μm) | ◎ | P13 |
| 104 | 0 | 1 | 2 | 22 | 25 | 24 | 19 | 5 | 2 | centrifugal airflow classification (125 μm) | ◎ | |
| 105 | 0 | 2 | 5 | 25 | 29 | 18 | 13 | 6 | 2 | centrifugal wet classification (125 μm) | ◎ | |

Gas sensor sample #99 has a powder filler containing a wide variety of grains whose grain size ranging from 'below 80 μm' to 'above 5000 μm'. Gas sensor sample #99 is not subjected to any classification.

Gas sensor samples #100 to #103 have powder fillers subjected to the dry sieving classification in which the aperture size is set to 40 μm, 80 μm, 100 μm and 125 μm for respective samples #100 to #103. Through the sieving classification, fine grains were removed from respective powder fillers. As a result, all of the gas sensor samples #100 to #103 contain fine grains whose weight percentage is less than that of the gas sensor sample #99.

Gas sensor sample #104 has a powder filler subjected to the centrifugal airflow classification to remove the fine grains of 80 μm or less.

Gas sensor sample #105 has a powder filler subjected to the centrifugal wet classification to remove the fine grains of 80 μm or less.

Next, the influence of removing coarse grains from the powder filler was checked by evaluating several gas sensor samples in the following manner.

Gas sensor sample #106 has a powder filler containing a wide variety of grains whose grain size ranging from 'below 80 μm' to 'above 5000 μm'. Gas sensor sample #106 is not subjected to any classification.

Gas sensor samples #107 to #109 have powder fillers subjected to the dry sieving classification in which the aperture size is set to 5,000 μm, 1,000 μm, and 710 μm for respective samples #107 to #109. Through the sieving classification, coarse grains were removed from respective powder fillers. As a result, all of the gas sensor samples #107 to #109 contain coarse grains whose weight percentage is less than that of the gas sensor sample #106.

Gas sensor sample #110 has a powder filler subjected to the centrifugal airflow classification to remove the coarse grains of 810 μm or above.

Gas sensor sample #111 has a powder filler subjected to the centrifugal wet classification to remove the coarse grains of 1,000 μm or above.

Table 4 shows the distribution of grains, the classification method, evaluation result, and the type of grain size distribution of respective tested gas sensor samples #106 to #111.

Due to the presence of a great amount of coarse grains, gas sensor sample #106 has poor gasoline sealing properties and accordingly has caused a large sensor output deterioration.

Other gas sensor samples #107 to #111 have relatively good gasoline sealing properties (evaluated ○ or ⊚). From this fact, it is confirmed that removing the coarse grains is effective to obtain a powder filler having excellent gasoline sealing properties.

From the comparison between #107 and other samples #108~#111, it is understood that removing the coarse grains having the grain size of 5,000 μm or above is very effective to enhance the gasoline sealing properties.

primary phosphate, the gas sensor samples #27 to #31 are evaluated excellent (⊚) as each having demonstrated a small sensor output reduction. Both of the gas sensor samples #26 to #32 have shown a relatively large sensor output reduction, although the evaluation is not bad (○).

Among the gas sensor samples #33 to #37 using the water solution of sodium silicate, the gas sensor samples #35 and #36 are evaluated excellent (⊚) as each having demonstrated a small sensor output reduction. The gas sensor sample #34 has also demonstrated excellent properties although it is inferior to the gas sensor samples #35 to #36. The remaining gas sensor samples #33 and #37 have shown a relatively large sensor output reduction, although the evaluation is not bad (○).

Among the gas sensor samples #38 to #42 using the water solution of potassium silicate, the gas sensor samples #40 and #41 are evaluated excellent (⊚) as each having demonstrated a small sensor output reduction. The gas sensor sample #39 has also demonstrated excellent properties

TABLE 4

| | Distribution (weight %) of Grains with respect to Grain Diameter (μm) | | | | | | | | | Method of classification | Evaluation | Type of Grain Size Distri. |
|---|---|---|---|---|---|---|---|---|---|---|---|---|
| Sample No. | ~80 | 80~100 | 100~125 | 125~250 | 250~710 | 710~810 | 810~1000 | 1000~5000 | 5000~ | | | |
| 106 | 1 | 3 | 5 | 10 | 11 | 12 | 13 | 15 | 30 | Nothing | X | P14 |
| 107 | 1 | 3 | 6 | 16 | 18 | 18 | 20 | 16 | 2 | dry sieving classification (aperture 5000 μm) | ○ | |
| 108 | 1 | 3 | 6 | 25 | 25 | 20 | 18 | 2 | 0 | dry sieving classification (aperture 1000 μm) | ⊚ | |
| 109 | 1 | 3 | 7 | 40 | 48 | 1 | 0 | 0 | 0 | dry sieving classification (aperture 710 μm) | ⊚ | P15 |
| 110 | 1 | 3 | 6 | 45 | 44 | 1 | 0 | 0 | 0 | centrifugal airflow classification (710 μm) | ⊚ | |
| 111 | 1 | 3 | 6 | 44 | 40 | 5 | 1 | 0 | 0 | centrifugal wet classification (125 μm) | ⊚ | |

Evaluation of several supplementary filler agents was conducted in the following manner.

As shown in Table 5, the powder filler used in this performance test is talc powder. The supplementary filler agent for gas sensor samples #26 to #32 is water solution of aluminum primary phosphate. The supplementary filler agent for gas sensor samples #33 to #37 is water solution of sodium silicate. The supplementary filler agent for gas sensor samples #38 to #42 is water solution of potassium silicate. The supplementary filler agent for gas sensor sample #43 is a mixture of the water solution of aluminum primary phosphate and the water solution of sodium silicate. The supplementary filler agent for gas sensor sample #44 is a mixture of water solution of aluminum primary phosphate and the water solution of potassium silicate. All of the tested supplementary filler agents are water solutions of inorganic compounds which are in a liquid state at the room temperature (20° C.).

In this table, the additive amount of each supplementary filler agent is expressed in terms of weight part relative to 100 weight part of the powder filler.

As understood from Table 5, among the gas sensor samples #26 to #32 using the water solution of aluminum although it is inferior to the gas sensor samples #40 to #41. The remaining gas sensor samples #38 and #42 have shown a relatively large sensor output reduction, although the evaluation is not bad (○).

As understood from the evaluation result shown in Table 5, aluminum primary phosphate, sodium silicate, and potassium silicate are preferable supplementary filler agents capably of letting the powder filler possess excellent gasoline sealing properties. The liquid supplementary filler agent smoothly penetrates into the clearances of grains when a pressing force is applied on the powder filler so as to obtain a highly densified filler.

Furthermore, it is apparent from Table 5 that a preferable additive range of the supplementary filler agent is in the range from 0.1 to 10 weight part.

The supplementary filler agent of gas sensor sample #43 contains the water solution of aluminum primary phosphate and the water solution of sodium silicate by the weight part ratio of 1:1. The supplementary filler agent of gas sensor sample #44 contains the water solution of aluminum primary phosphate and the water solution of potassium silicate by the weight part ratio of 1:1. Both of the gas sensor samples #43 and #44 have demonstrated excellent properties.

In this manner, it is preferable to use a mixture of different kinds of additives as a supplementary filler agent for the powder, filler.

TABLE 5

| Sample No. | Supplementary Filler Agent | Additive Amount (Weight Part) | Powder Filler | Evaluation |
|---|---|---|---|---|
| 26 | water solution of aluminum primary phosphate | 0.05 | talc | ○ |
| 27 | | 0.1 | | ◎ |
| 28 | | 1 | | ◎ |
| 29 | | 2 | | ◎ |
| 30 | | 5 | | ◎ |
| 31 | | 10 | | ◎ |
| 32 | | 15 | | ○ |
| 33 | water solution of sodium silicate | 0.05 | | ○ |
| 34 | | 0.1 | | ○ |
| 35 | | 2 | | ◎ |
| 36 | | 10 | | ◎ |
| 37 | | 15 | | ○ |
| 38 | water solution of potassium silicate | 0.05 | | ○ |
| 39 | | 0.1 | | ○ |
| 40 | | 2 | | ◎ |
| 41 | | 10 | | ◎ |
| 42 | | 15 | | ○ |
| 43 | water solution of aluminum primary phosphate + | 1 + 1 | | ◎ | lime-alumino group glass. The supplementary filler agent for gas sensor sample #56 is aluminate glass. All of the tested supplementary filler agents are solid inorganic compounds which are liquefiable at the temperature of 600° C. or less.

In this table, the additive amount of each supplementary filler agent is expressed in terms of weight part relative to 100 weight part of the powder filler.

As understood from Table 6, among the gas sensor samples #45 to #49 using barium hydroxide, the gas sensor samples #46 to #48 are evaluated excellent (◎) especially as each having demonstrated a small sensor output reduction and therefore having excellent gasoline sealing properties. Both of gas sensor samples #45 and #49 have shown a relatively large sensor output reduction, although the evaluation is not bad (○). In other words, adding the supplementary filler agent too much or too less is not preferable to obtain excellent properties.

Furthermore, the remaining gas sensor samples #50 to #56 using different kinds of inorganic compounds are evaluated excellent (◎) especially as each having demonstrated a small sensor output reduction and therefore having excellent gasoline sealing properties.

TABLE 6

| Sample No. | Supplementary Filler Agent | | Additive Amount (Weight Part) | Evaluation |
|---|---|---|---|---|
| 45 | barium hydroxide | $Ba(OH)_2 \cdot 8H_2O$ | 0.3 | ○ |
| 46 | | | 0.5 | ◎ |
| 47 | | | 10 | ◎ |
| 48 | | | 30 | ◎ |
| 49 | | | 40 | ○ |
| 50 | borosilicate glass | $Na_2O$—$Al_2O_3$—$B_2O_3$—$SiO_2$ | 5 | ◎ |
| 51 | aluminosilicate glass | $CaO$—$BaO$—$MgO$—$Al_2O_3$—$SiO_2$ | 5 | ◎ |
| 52 | soda-lime silicate glass | $Na_2O$—$CaO$—$Al_2O_3$—$SiO_2$ | 5 | ◎ |
| 53 | lead silicate glass | $PbO$—$Na_2O$—$SiO_2$ | 5 | ◎ |
| 54 | low-melting borate glass | $PbO(Bi_2O_3)$—$ZnO$—$B_2O_3$ | 5 | ◎ |
| 55 | lime-alumino group glass | $CaO$—$Al_2O_3$—$ZnO$—$SiO_2$ | 5 | ◎ |
| 56 | aluminate glass | $CaO$—$Al_2O_3$—$ZnO$—$B_2O_3$—$SiO_2$ | 5 | ◎ |

TABLE 5-continued

| Sample No. | Supplementary Filler Agent | Additive Amount (Weight Part) | Powder Filler | Evaluation |
|---|---|---|---|---|
| 44 | water solution of sodium silicate water solution of aluminum primary phosphate + water solution of potassium silicate | 1 + 1 | | ◎ |

Similarly, evaluation of other supplementary filler agents was conducted in the following manner.

Figure 5:
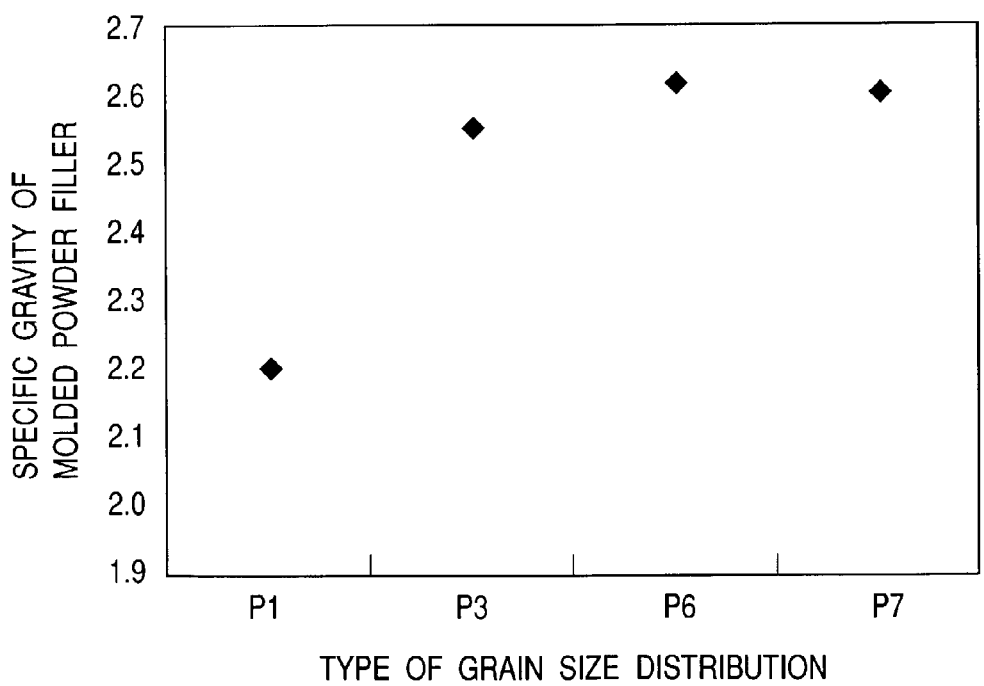
FIG. 5 is a graph showing the relationship between specific gravity of molded powder filler and type of grain size.

As shown in Table 6, the powder filler used in this performance test is talc powder. The supplementary filler agent for gas sensor samples #45 to #49 is barium hydroxide. The supplementary filler agent for gas sensor sample #50 is borosilicate glass. The supplementary filler agent for gas sensor sample #51 is aluminosilicate glass. The supplementary filler agent for gas sensor sample #52 is soda-lime silicate glass. The supplementary filler agent for gas sensor sample #53 is lead silicate glass. The supplementary filler agent for gas sensor sample #54 is low-melting borate glass. The supplementary filler agent for gas sensor sample #55 is FIG. 5 shows the distribution of specific gravity of tested powder fillers which are molded by adding a pressing force onto the powder material.

As apparent from the above-described Table 1, type P1 represents the grain size distribution concentrated chiefly on very small diameters. The powder filler of type P1 has a smaller specific gravity compared with others. Accordingly, a gas sensor will have poor gasoline sealing properties if the powder filler of type P1 is stuffed in the filler space. On the contrary, the powder fillers classified into the types P3, P6 and P7 have higher specific gravities. A gas sensor will have excellent gasoline sealing properties if the powder filler of type P3, P6 or P7 is stuffed in the filler space (refer to Tables 1 and 2).

FIGS. 6 to 11 are view explaining the positional relationship between the axial length of the filler space 14 and the uneven surficial layer 203 or the electrode protecting layer 205.

Figure 9:
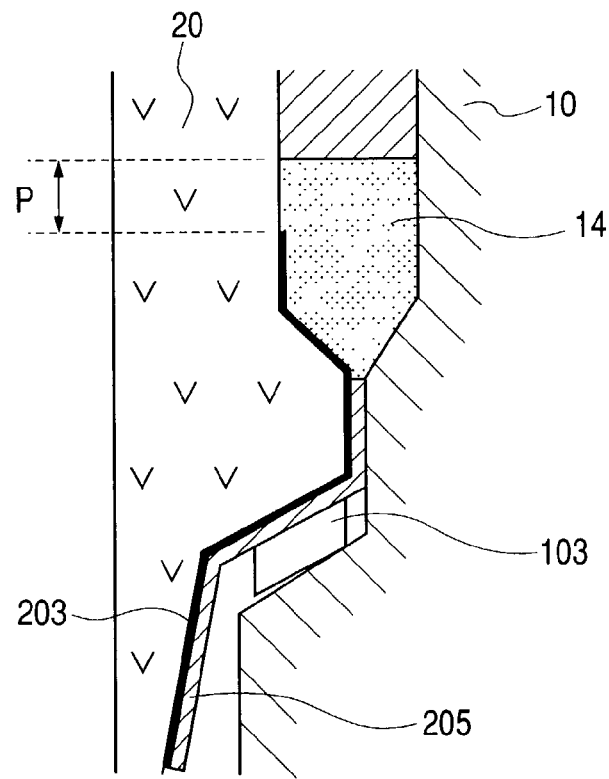
FIG. 9 is a view showing a gas sensor which is dimensionally characterized N=0 as a preferred embodiment of the present invention.
Figure 10:
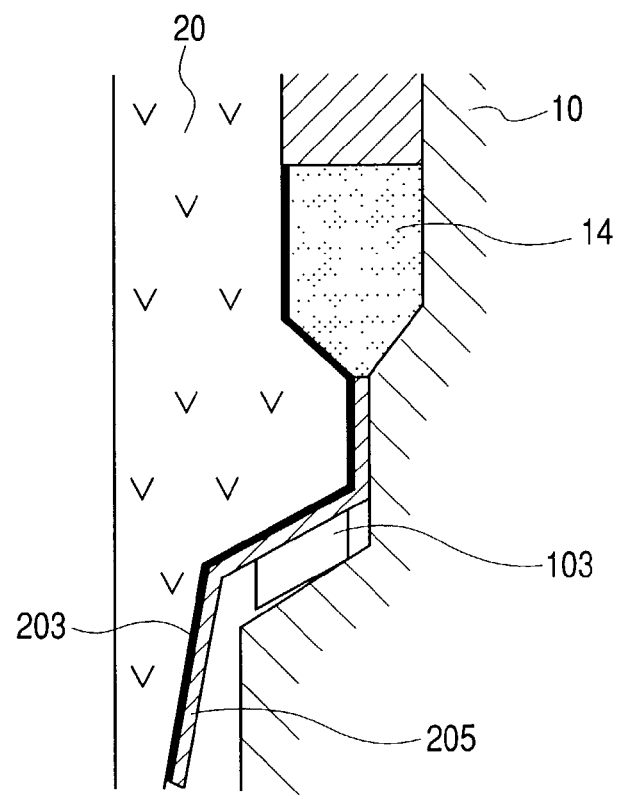
FIG. 10 is a view showing a gas sensor which is dimensionally characterized by N=0 and L=M as a preferred embodiment of the present invention.
Figure 11:
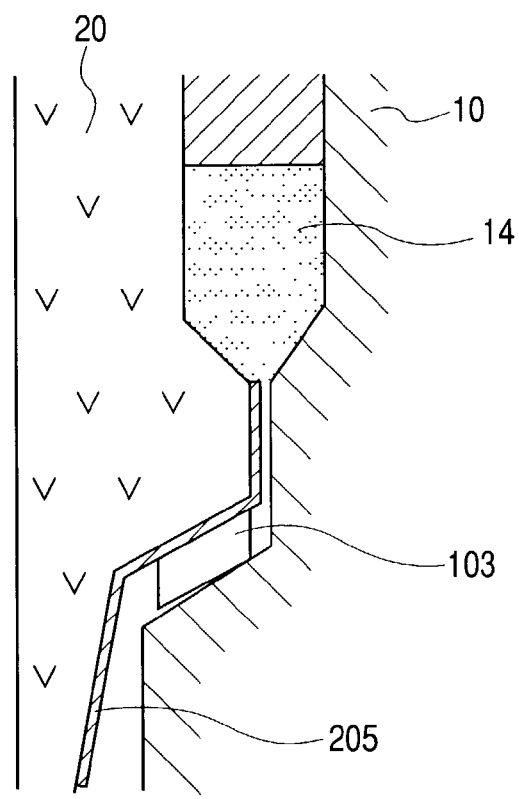
FIG. 11 is a view showing a gas sensor which has no uneven surficial layer and is dimensionally characterized by N=0 as a preferred embodiment of the present invention.

As shown in FIGS. 6 to 11, the uneven surficial layer 203 is provided on the outer surface of solid electrolytic body 20. Although not shown in the drawings, an outside electrode is provided extensively so as to cover the uneven surficial layer 203. FIG. 11 shows a gas sensor having no uneven surficial layer.

In each of FIGS. 6 to 11, the filler space 14 is provided between the solid electrolytic body 20 and the housing 10. The length L represents an axial length of filler space 14 which extends in the axial direction from a distal end (i.e., lower end) 141 to a proximal end (i.e., upper end) 142.

The length M represents an axial length of uneven surficial layer 203 in the filler space 14. The length M is defined as a vertical (i.e., axial) distance from the proximal end (i.e., upper end) of uneven surficial layer 203 to the distal end (i.e., lower end) 141 of filler space 14.

Similarly, length N represents an axial length of electrode protecting layer 205 in the filler space 14. The length N is defined as a vertical (i.e., axial) distance from a proximal end (i.e., upper end) of electrode protecting layer 205 to the distal end (i.e., lower end) 141 of filler space 14.

Figure 6:
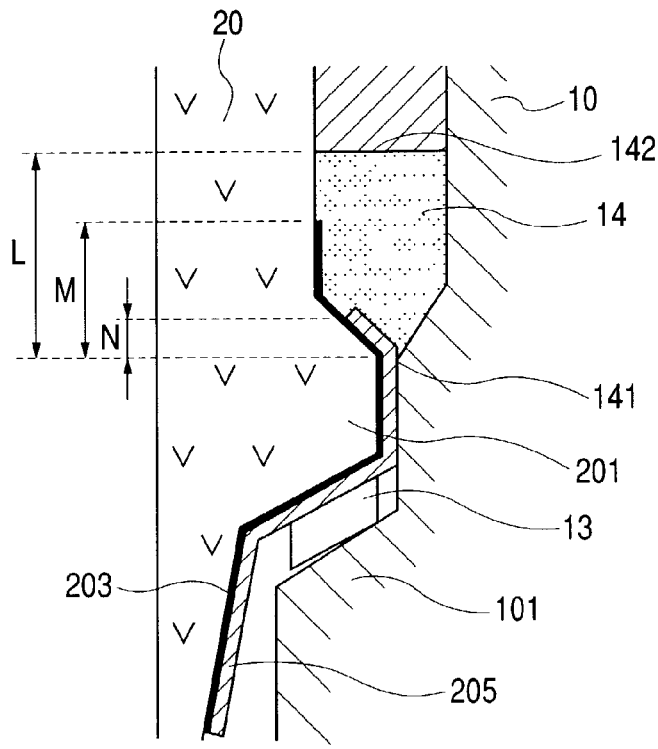
FIG. 6 is a view showing the dimensional relationship among axial length L of a filler space, axial length M of an uneven surficial layer in the filler space, and axial length N of an electrode protecting layer of a gas sensor in accordance with a preferred embodiment of the present invention.

FIG. 6 shows a gas sensor which is dimensionally characterized by L>M>N.

Figure 7:
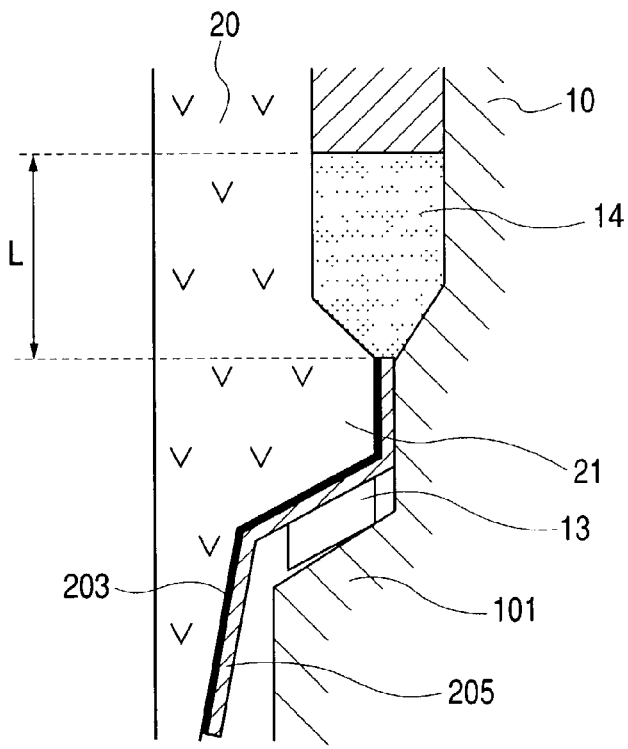
FIG. 7 is a view showing a gas sensor which is dimensionally characterized by M=N=0 as a preferred embodiment of the present invention.

FIG. 7 shows a gas sensor which is dimensionally characterized by M=N=0 and L=4 mm. The proximal end (i.e., upper end) of uneven surficial layer 203 and the proximal end (i.e., upper end) of electrode protecting layer 205 are identical with the distal end (i.e., lower end) of filler space 14.

Figure 8:
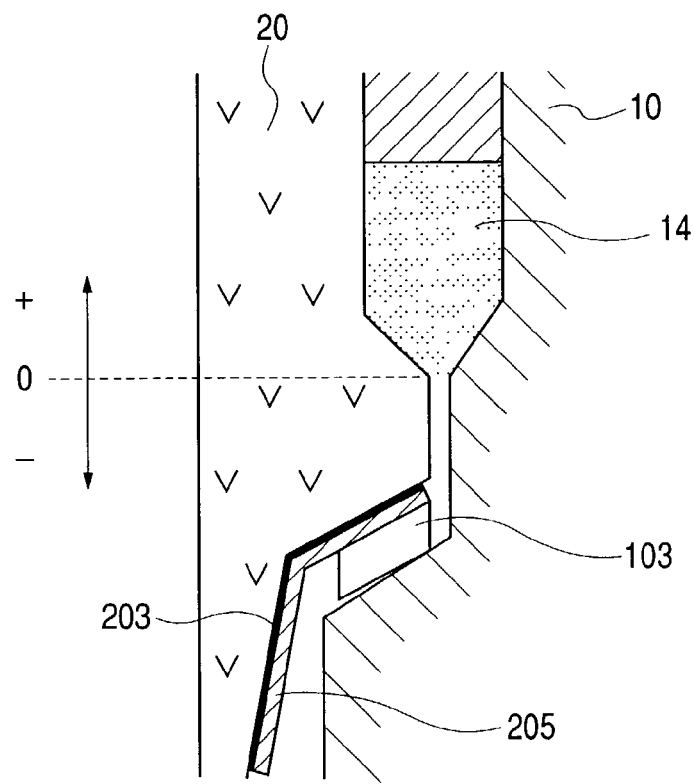
FIG. 8 is a view showing a gas sensor which is dimensionally characterized by M=N=−1 mm as a preferred embodiment of the present invention.

FIG. 8 shows a gas sensor which is dimensionally characterized by M=N=−1 mm and L=4 mm. In this case, the proximal end (i.e., upper end) of uneven surficial layer 203 and the proximal end (i.e., upper end) of electrode protecting layer 205 are offset lower than the distal end (i.e., lower end) 141 of filler space 14 by an amount of 1 mm. As shown in FIG. 8, the distal end 141 of filler space 14 is the origin (=0) in the altitudinal direction. The proximal end side (i.e., upper side) is expressed by a positive (+) value with respect to the origin, while the distal end side (i.e., lower side) is expressed by a negative (−) value with respect to the origin.

FIG. 9 shows a gas sensor which is dimensionally characterized by N=0 mm, L=4 mm and M=3.5 mm. The proximal end (i.e., upper end) of uneven surficial layer 203 is offset lower than the proximal end (i.e., upper end) 142 of filler space 14 by a distance P of 0.5 mm.

FIG. 10 shows a gas sensor which is dimensionally characterized by N=0 mm and L=M=4 mm. The uneven surficial layer 203 is fully extended to the proximal end (i.e., upper end) 142 of filler space 14.

FIG. 11 shows a gas sensor which has no uneven surficial layer and is dimensionally characterized by L=4 mm and N=0 mm. The proximal end (i.e., upper end) of electrode protecting layer 205 is identical with the distal end (i.e., lower end) 141 of filler space 14.

The gas sensor performance was evaluated in relation to the axial lengths of the uneven surficial layer and the electrode protecting layer.

As shown in Table 7, all of the tested gas sensor samples #57 to #70 are differentiated in the dimensions of the uneven surficial layer and the electrode protecting layer, although these samples #57 to #70 have the same axial length of 4 mm.

The gas sensor samples #60, #64 and #67 were evaluated as having bad performance.

The gas sensor sample #60 has an uneven surficial layer of 5 mm which protrudes upward from the proximal end (i.e., upper end) of the filler space. In this case, due to its surface roughness, the uneven surficial layer serves as an immersion path (chiefly consisting of micro holes and clearances) which allows the liquid (gasoline) to enter into the air atmosphere beyond the powder filler.

The gas sensor sample #64 has an electrode protecting layer of 5 mm which protrudes upward from the proximal end (i.e., upper end) of the filler space. In this case, the electrode protecting layer has an uneven surface. The electrode protecting layer serves as an immersion path (chiefly consisting of micro holes and clearances) which allows the liquid (gasoline) to enter into the air atmosphere beyond the powder filler.

The gas sensor sample #67 has an uneven surficial layer of 5 mm and an electrode protecting layer of 5 mm both of which protrude upward from the proximal end (i.e., upper end) of the filler space and accordingly serve as the immersion path (chiefly consisting of micro holes and clearances) which allows the liquid to enter into the air atmosphere beyond the powder filler.

TABLE 7

| Sample No. | Axial Length of Filler Space (mm) | Axial Length of Uneven Surficial Layer (mm) | Axial Length of Electrode Protecting Layer (mm) | Evaluation |
| --- | --- | --- | --- | --- |
| 57 | 4 | 0 | 0 | ⊚ |
| 58 | | 3.5 | 0 | ⊚ |
| 59 | | 4 | 0 | ◯ |
| 60 | | 5 | 0 | X |
| 61 | | 0 | 0 | ⊚ |
| 62 | | 0 | 3.5 | ⊚ |
| 63 | | 0 | 4 | ◯ |
| 64 | | 0 | 5 | X |
| 65 | | 3.5 | 3.5 | ⊚ |
| 66 | | 4 | 4 | ◯ |
| 67 | | 5 | 5 | X |
| 68 | | −1 | 0 | ⊚ |
| 69 | | 0 | −1 | ⊚ |
| 70 | | −1 | −1 | ⊚ |

The gas sensor performance was evaluated in relation to the presence of fine or coarse grains contained in the powder filler.

As shown in Tables 8 and 9, gas sensor samples #113, #121, and #125 have powder fillers containing a wide variety of grains whose grain size ranging from 'below 80 μm' to 'above 5000 μm'. Gas sensor samples #113, #121, and #125 are not subjected to any classification.

Gas sensor samples #114 to #120 have powder fillers subjected to the dry sieving classification to remove fine and coarse grains from the powder filler of gas sample #113. The powder filler of gas sensor sample #114 is subjected to the dry sieving classification in which the aperture size is set to 40 μm for removing fine grains and set to 5,000 μm for removing coarse grains. The powder filler of gas sensor sample #115 is subjected to the dry sieving classification in which the aperture size is set to 80 μm for removing fine grains and set to 5,000 μm for removing coarse grains. The powder filler of gas sensor sample #116 is subjected to the dry sieving classification in which the aperture size is set to 80 μm for removing fine grains and set to 1,000 μm for removing coarse grains. The powder filler of gas sensor sample #117 is subjected to the dry sieving classification in which the aperture size is set to 80 μm for removing fine grains and set to 710 μm for removing coarse grains. The powder filler of gas sensor sample #118 is subjected to the dry sieving classification in which the aperture size is set to 100 μm for removing fine grains and set to 1,000 μm for removing coarse grains. The powder filler of gas sensor sample #119 is subjected to the dry sieving classification in which the aperture size is set to 125 μm for removing fine grains and set to 5,000 μm for removing coarse grains. And, the powder filler of gas sensor sample #120 is subjected to the dry sieving classification in which the aperture size is set to 125 μm for removing fine grains and set to 710 μm for removing coarse grains.

Gas sensor samples #122 to #124 have powder fillers subjected to the dry sieving classification to remove fine and coarse grains from the powder filler of gas sample #121. The powder filler of gas sensor sample #122 is subjected to the dry sieving classification in which the aperture size is set to 40 μm for removing fine grains and set to 5,000 μm for removing coarse grains. The powder filler of gas sensor sample #123 is subjected to the dry sieving classification in which the aperture size is set to 100 μm for removing fine grains and set to 1,000 μm for removing coarse grains. And, the powder filler of gas sensor sample #124 is subjected to the dry sieving classification in which the aperture size is set to 125 μm for removing fine grains and set to 710 μm for removing coarse grains.

Gas sensor samples #126 to #128 have powder fillers subjected to the dry sieving classification to remove fine and coarse grains from the powder filler of gas sample #125. The powder filler of gas sensor sample #126 is subjected to the dry sieving classification in which the aperture size is set to 40 μm for removing fine grains and set to 5,000 μm for removing coarse grains. The powder filler of gas sensor sample #127 is subjected to the dry sieving classification in which the aperture size is set to 100 μm for removing fine grains and set to 1,000 μm for removing coarse grains. And, the powder filler of gas sensor sample #128 is subjected to the dry sieving classification in which the aperture size is set to 125 μm for removing fine grains and set to 710 μm for removing coarse grains.

The powder filler of gas sensor sample #129 is subjected to the centrifugal airflow classification to remove the fine grains of 80 μm or less and the coarse grains of 5,000 μm or above. The powder filler of gas sensor sample #130 is subjected to the centrifugal wet classification to remove the fine grains of 80 μm or less and the coarse grains of 5,000 μm or above.

Due to the presence of a great amount of fine and coarse grains, all of the gas sensor samples #113, #121, and #125 have poor gasoline sealing properties and accordingly have caused large sensor output deteriorations.

Other gas sensor samples #114~#120, #122~#124, and #126~#128 have relatively good gasoline sealing properties (evaluated ○ or ⊙). From this fact, it is confirmed that removing the fine and coarse grains is effective to obtain a powder filler having excellent gasoline sealing properties.

The properties of gas sensor samples #114, #122, and #126 are inferior to other gas sensor samples #115~#120, #123, #124, #127, and #128 because these samples #114, #122, and #126 contain a relatively large amount of fine and coarse grains.

TABLE 8

| Sample No. | Distribution (weight %) of Grains with respect to Grain Diameter (μm) | | | | | | | | |
|---|---|---|---|---|---|---|---|---|---|
| | ~80 | 80~100 | 100~125 | 125~250 | 250~710 | 710~810 | 810~1000 | 1000~5000 | 5000~ |
| 113 | 15 | 12 | 10 | 10 | 11 | 10 | 10 | 7 | 15 |
| 114 | 10 | 11 | 12 | 14 | 15 | 14 | 12 | 10 | 2 |
| 115 | 9 | 12 | 12 | 14 | 15 | 14 | 12 | 10 | 2 |
| 116 | 8 | 12 | 14 | 17 | 19 | 16 | 12 | 2 | 0 |
| 117 | 8 | 18 | 22 | 24 | 26 | 2 | 0 | 0 | 0 |
| 118 | 2 | 7 | 15 | 19 | 21 | 19 | 15 | 2 | 0 |
| 119 | 0 | 2 | 6 | 19 | 21 | 22 | 18 | 10 | 2 |
| 120 | 0 | 2 | 5 | 43 | 48 | 2 | 0 | 0 | 0 |
| 121 | 30 | 10 | 11 | 12 | 13 | 11 | 10 | 2 | 1 |
| 122 | 9 | 11 | 15 | 16 | 17 | 15 | 11 | 4 | 2 |
| 123 | 1 | 8 | 17 | 22 | 21 | 18 | 12 | 1 | 0 |
| 124 | 1 | 1 | 3 | 72 | 21 | 2 | 0 | 0 | 0 |
| 125 | 1 | 2 | 4 | 7 | 11 | 13 | 15 | 18 | 29 |
| 126 | 1 | 2 | 8 | 14 | 15 | 18 | 16 | 24 | 2 |
| 127 | 1 | 2 | 11 | 22 | 24 | 18 | 20 | 2 | 0 |
| 128 | 1 | 1 | 4 | 42 | 50 | 2 | 0 | 0 | 0 |
| 129 | 0 | 1 | 2 | 51 | 45 | 1 | 0 | 0 | 0 |
| 130 | 0 | 2 | 6 | 46 | 38 | 7 | 1 | 0 | 0 |

TABLE 9

| Sample No. | Method of Classification | | Evaluation | Type of Grain Size Distribution |
|---|---|---|---|---|
| 113 | nothing | | X | P16 |
| 114 | dry sieving classification | apertures 40 μm & 5000 μm | ○ | |
| 115 | dry sieving classification | apertures 80 μm & 5000 μm | ⊙ | |
| 116 | dry sieving classification | apertures 80 μm & 1000 μm | ⊙ | |
| 117 | dry sieving classification | apertures 80 μm & 710 μm | ⊙ | |
| 118 | dry sieving classification | apertures 100 μm & 1000 μm | ⊙ | |
| 119 | dry sieving classification | apertures 125 μm & 5000 μm | ⊙ | |
| 120 | dry sieving classification | apertures 125 μm & 710 μm | ⊙ | P17 |
| 121 | nothing | | X | P18 |
| 122 | dry sieving classification | apertures 40 μm & 5000 μm | ○ | |
| 123 | dry sieving classification | apertures 100 μm & 1000 μm | ⊙ | |
| 124 | dry sieving classification | apertures 125 μm & 710 μm | ⊙ | P19 |
| 125 | nothing | | X | P20 |
| 126 | dry sieving classification | apertures 40 μm & 5000 μm | ○ | |
| 127 | dry sieving classification | apertures 100 μm & 1000 μm | ⊙ | |

TABLE 9-continued

| Sample No. | Method of Classification | | Evaluation | Type of Grain Size Distribution |
|---|---|---|---|---|
| 128 | dry sieving classification | apertures 125 μm & 710 μm | ◎ | P21 |
| 129 | centrifugal airflow classification | 125 μm & 710 μm | ◎ | |
| 130 | centrifugal wet classification | 125 μm & 710 μm | ◎ | |

The gas sensor performance was evaluated in relation to the type of grain size distribution in the powder filler as well as in relation to the additive amount of the supplementary filler agent.

As shown in Table 10, all of the tested gas sensor samples #71~#77 and #131~#136 are differentiated in the type of grain size distribution and the additive amount of the supplementary filler agent, although these samples #71~#77 and #131~#136 have the same powder filler (talc) and use the same supplementary filler agent (water solution of aluminum primary phosphate).

The gas sensor samples #72~#76, #132, #134 and #136 were evaluated as having excellent gasoline sealing properties (◎).

The powder filler of gas sensor sample #71 contains a great amount of fine grains (type P1), although the evaluation is not bad (○). On the contrary, the powder filler of gas sensor sample #77 contains a great amount of coarse grains (type P10), although the evaluation is not bad (◎). Both of the gas sensor samples #71 and #77 have shown gasoline sealing properties inferior to those of the gas sensor samples #72 to #76.

The powder filler of gas sensor sample #131 contains a great amount of fine and coarse grains (type P16), although the evaluation is not bad (○). The powder filler of gas sensor sample #133 contains a great amount of fine grains (type P18), although the evaluation is not bad (○).

The powder filler of gas sensor sample #135 contains a great amount of coarse grains (type P20), although the evaluation is not bad (○). As apparent from the evaluation result of Table 10, the fine and coarse grains contained in the powder filler significantly worsen the gasoline sealing properties of a gas sensor.

The gas sensor performance was evaluated in relation to the type of grain size distribution in the powder filler as well as in relation to the axial lengths of the uneven surficial layer and the electrode protecting layer.

As shown in Table 11, all of the tested gas sensor samples #78~#84 and #137~#142 are differentiated in the type of grain size distribution and also in the dimensions of the uneven surficial layer and the electrode protecting layer, although these samples #78~#84 and #137~#142 have the same powder filler (talc).

The gas sensor samples #79~#83, #138, #140, and #142 were evaluated as having excellent gasoline sealing properties (◎).

The gasoline sealing properties of gas sensor sample #78 is not so excellent because the powder filler contains a great amount of fine grains (type P1). The gasoline sealing properties of gas sensor sample #84 is not so excellent because the powder filler contains a great amount of coarse grains (type P10). The gasoline sealing properties of gas sensor sample #137 is not so excellent because the powder filler contains a great amount of fine and coarse grains (type P16). The gasoline sealing properties of gas sensor sample #139 is not so excellent because the powder filler contains a great amount of coarse grains (type P18). And, the gasoline sealing properties of gas sensor sample #141 is not so excellent because the powder filler contains a great amount of coarse grains (type P20).

All of the gas sensor samples #78, #84, #137, #139, and #141 have the axial lengths of the uneven surficial layer and the electrode protecting layer which are identical with the axial length of the filler space. This dimensional relationship gives adverse influence to the gasoline sealing properties.

TABLE 10

| Sample No. | Type of Grain Size Distribution | Axial Length of Filler Space (mm) | Powder Filler | Supplementary Filler Agent | Additive Amount (Weight Part) | Evaluation |
|---|---|---|---|---|---|---|
| 71 | P1 | 4 | talc | water solution of aluminum primary phosphate | 0.05 | ○ |
| 72 | P3 | | | | 2 | ◎ |
| 73 | P6 | | | | 0.1 | ◎ |
| 74 | P6 | | | | 2 | ◎ |
| 75 | P6 | | | | 10 | ◎ |
| 76 | P8 | | | | 2 | ◎ |
| 77 | P10 | | | | 0.05 | ○ |
| 131 | P16 | | | | 0.05 | ○ |
| 132 | P17 | | | | 2 | ◎ |
| 133 | P18 | | | | 0.05 | ○ |
| 134 | P19 | | | | 2 | ◎ |
| 135 | P20 | | | | 0.05 | ○ |
| 136 | P21 | | | | 2 | ◎ |

TABLE 11

| Sample No. | Type of Grain Size Distribution | Axial Length of Filler Space (mm) | Powder Filler | Axial Length of Uneven Surficial Layer (mm) | Axial Length of Electrode Protecting Layer (mm) | Evaluation |
|---|---|---|---|---|---|---|
| 78 | P1 | 4 | talc | 4 | 4 | ○ |
| 79 | P3 | | | 0 | 0 | ◎ |
| 80 | P4 | | | 2 | 2 | ◎ |
| 81 | P6 | | | 0 | 0 | ◎ |
| 82 | P6 | | | 2 | 2 | ◎ |
| 83 | P8 | | | 2 | 2 | ◎ |
| 84 | P10 | | | 4 | 4 | ○ |
| 137 | P16 | | | 4 | 4 | ○ |
| 138 | P17 | | | 2 | 2 | ◎ |
| 139 | P18 | | | 4 | 4 | ○ |
| 140 | P19 | | | 2 | 2 | ◎ |
| 141 | P20 | | | 4 | 4 | ○ |
| 142 | P21 | | | 2 | 2 | ◎ |

The gas sensor performance was evaluated in relation to the additive amount of the supplementary filler agent as well as in relation to the axial lengths of the uneven surficial layer and the electrode protecting layer.

As shown in Table 12, all of the tested gas sensor samples #85 to #91 are differentiated in the additive amount of the supplementary filler agent and also in the dimensions of the uneven surficial layer and the electrode protecting layer, although these samples #85 to #91 have the same powder filler (talc) and uses the same supplementary filler agent (water solution of aluminum primary phosphate).

The gas sensor samples #86 to #90 were evaluated as having excellent gasoline sealing properties (◎).

The gas sensor sample #85 is inferior to the gas sensor samples #86 to #90 in the gasoline sealing properties because the additive amount of the supplementary filler agent is small and also because the axial lengths of the uneven surficial layer and the electrode protecting layer are identical with the axial length of the filler space.

The gas sensor sample #91 is inferior to the gas sensor samples #86 to #90 in the gasoline sealing properties because the additive amount of the supplementary filler agent is large and also because the axial lengths of the uneven surficial layer and the electrode protecting layer are identical with the axial length of the filler space.

axial lengths of the uneven surficial layer and the electrode protecting layer.

As shown in Table 13, all of the tested gas sensor samples #92 to #98 are differentiated in the type of size distribution, in the additive amount of the supplementary filler agent, and in the dimensions of the uneven surficial layer and the electrode protecting layer, although these samples #92 to #98 have the same powder filler (talc) and uses the same supplementary filler agent (water solution of aluminum primary phosphate).

The gas sensor samples #93 to #97 were evaluated as having excellent gasoline sealing properties (◎).

The gas sensor sample #92 is inferior to the gas sensor samples #93 to #97 in the gasoline sealing properties because the powder filler contains a great amount of small grains (type P1) and because the additive amount of the supplementary filler agent is small and also because the axial lengths of the uneven surficial layer and the electrode protecting layer are identical with the axial length of the filler space.

The gas sensor sample #98 is inferior to the gas sensor samples #93 to #97 in the gasoline sealing properties because the powder filler contains a great amount of large grains (type P10) and because the additive amount of the supplementary filler agent is small and also because the axial

TABLE 12

| Sample No. | Axial Length of Filler Space (mm) | Powder Filler | Supplementary Filler Agent | Additive Amount (Weight Part) | Axial Length of Uneven Surficial Layer (mm) | Axial Length of Electrode Protecting Layer (mm) | Evaluation |
|---|---|---|---|---|---|---|---|
| 85 | 4 | talc | water solution of aluminum primary phosphate | 0.05 | 4 | 4 | ○ |
| 86 | | | | 0.1 | 2 | 2 | ◎ |
| 87 | | | | 2 | 0 | 0 | ◎ |
| 88 | | | | 2 | 2 | 2 | ◎ |
| 89 | | | | 2 | 4 | 4 | ◎ |
| 90 | | | | 10 | 2 | 2 | ◎ |
| 91 | | | | 15 | 4 | 4 | ○ |

The gas sensor performance was evaluated in relation to the type of grain size distribution in the powder filler, the additive amount of the supplementary filler agent, and the lengths of the uneven surficial layer and the electrode protecting layer are identical with the axial length of the filler space.

TABLE 13

| Sample No. | Type of Grain Size Distribution | Axial Length of Filler Space (mm) | Powder Filler | Supplementary Filler Agent | Additive Amount (Weight Part) | Axial Length of Uneven Surficial Layer (mm) | Axial Length of Electrode Protecting Layer (mm) | Evaluation |
|---|---|---|---|---|---|---|---|---|
| 92 | P1 | 4 | talc | water solution of aluminum primary phosphate | 0.05 | 4 | 4 | ○ |
| 93 | P3 | | | | 2 | 2 | 2 | ◎ |
| 94 | P6 | | | | 2 | 0 | 0 | ◎ |
| 95 | P6 | | | | 2 | 2 | 2 | ◎ |
| 96 | P6 | | | | 10 | 2 | 2 | ◎ |
| 97 | P8 | | | | 2 | 2 | 2 | ◎ |
| 98 | P10 | | | | 0.05 | 4 | 4 | ○ |

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A gas sensor comprising:
a housing;
a gas sensing element disposed in said housing;
a powder filler stuffed in a filler space defined between said housing and said gas sensing element so as to airtightly seal a clearance between said housing and said gas sensing element, wherein said powder filler contains grains whose diameter is in a range from 80 µm to 5,000 µm when measured before being stuffed into said filler space, and a weight percentage of said grains having the diameter of 80 µm to 5,000 µm is equal to or larger than 80% with respect to an overall weight of said powder filler;
an outside electrode disposed on a surface of said gas sensing element;
an electrode protecting layer provided on the surface of said gas sensing element so as to cover and protect said outside electrode; and
an uneven surficial layer for enhancing adhesion of said outside electrode to said electrode protecting layer and holding said outside electrode on the surface of said gas sensing element,
wherein proximal ends of said uneven surficial layer and the electrode protecting layer are offset toward a distal end side of said gas sensor with respect to said proximal end of said filler space, and
wherein said outside electrode extends toward a proximal end side of said gas sensor with respect to said proximal end of said filler space.

2. The gas sensor in accordance with claim 1, wherein said powder filler contains grains whose diameter is in a range from 100 µm to 1,000 µm when measured before being stuffed into said filler space and the weight percentage of the grains having the diameter of 100 µm to 1,000 µm is equal to or larger than 80% with respect to the overall weight of said powder filler.

3. The gas sensor in accordance with claim 1, wherein said powder filler contains grains whose diameter is in a range from 125 µm to 710 µm when measured before being stuffed into said filler space and the weight percentage of the grains having the diameter of 125 µm to 710 µm is equal to or larger than 80% with respect to the overall weight of said powder filler.

4. The gas sensor in accordance with claim 1, wherein an axial length of said filler space is in a range from 1.5 mm to 15 mm.

5. The gas sensor in accordance with claim 1, wherein said powder filler contains at least one of talc and boron nitride by an amount of 50 weight % or more.

6. A gas sensor comprising:
a housing;
a gas sensing element disposed in said housing;
a powder filler stuffed in a filler space defined between said housing and said gas sensing element so as to airtightly seal a clearance between said housing and said gas sensing element, wherein said powder filler contains grains which are subjected to a classification to remove fine grains before said powder filler is stuffed into said filler space;
an outside electrode disposed on a surface of said gas sensing element;
an electrode protecting layer provided on the surface of said gas sensing element so as to cover and protect said outside electrode; and
an uneven surficial layer for enhancing adhesion of said outside electrode to said electrode protecting layer and holding said outside electrode on the surface of said gas sensing element,
wherein proximal ends of said uneven surficial layer and the electrode protecting layer are offset toward a distal end side of said gas sensor with respect to said proximal end of said filler space, and
wherein said outside electrode extends toward a proximal end side of said gas sensor with respect to said proximal end of said filler space.

7. The gas sensor in accordance with claim 6, wherein said powder filler, after having been subjected to the classification, contains fine grains having a diameter equal to or less than 80 µm by a weight percentage equal to or less than 10% with respect to the overall weight of said powder filler.

8. The gas sensor in accordance with claim 6, wherein said powder filler, after having been subjected to the classification, contains fine grains having a diameter equal to or less than 100 µm by a weight percentage equal to or less than 10% with respect to the overall weight of said powder filler.

9. The gas sensor in accordance with claim 6, wherein said powder filler, after having been subjected to the classification, contains fine grains having a diameter equal to or less than 125 µm by a weight percentage equal to or less than 10% with respect to the overall weight of said powder filler.

10. The gas sensor in accordance with claim 6, wherein an axial length of said filler space is in a range from 1.5 mm to 15 mm.

11. The gas sensor in accordance with claim 6, wherein said powder filler contains at least one of talc and boron nitride by an amount of 50 weight % or more.

12. A gas sensor comprising:
a housing;
a gas sensing element disposed in said housing; and
a powder filler stuffed in a filler space defined between said housing and said gas sensing element so as to airtightly seal a clearance between said housing and said gas sensing element, wherein said powder filler contains grains which are subjected to a classification to remove coarse grains before said powder filler is stuffed into said filler space;
an outside electrode disposed on a surface of said gas sensing element;
an electrode protecting layer provided on the surface of said gas sensing element so as to cover and protect said outside electrode; and
an uneven surficial layer for enhancing adhesion of said outside electrode to said electrode protecting layer and holding said outside electrode on the surface of said gas sensing element,
wherein proximal ends of said uneven surficial layer and the protecting layer are offset toward a distal end side of said gas sensor with respect to said proximal end of said filler space, and
wherein said outside electrode extends toward a proximal end side of said gas sensor with respect to said proximal end of said filler space.

13. The gas sensor in accordance with claim 12, wherein said powder filler, after having been subjected to the classification, contains coarse grains having a diameter equal to or larger than 5,000 μm by a weight percentage equal to or less than 10% with respect to the overall weight of said powder filler.

14. The gas sensor in accordance with claim 12, wherein said powder filler, after having been subjected to the classification, contains coarse grains having a diameter equal to or larger than 1,000 μm by a weight percentage equal to or less than 10% with respect to the overall weight of said powder filler.

15. The gas sensor in accordance with claim 12, wherein said powder filler, after having been subjected to the classification, contains coarse grains having a diameter equal to or larger than 710 μm by a weight percentage equal to or less than 10% with respect to the overall weight of said powder filler.

16. The gas sensor in accordance with claim 12, wherein an axial length of said filler space is in a range from 1.5 mm to 15 mm.

17. The gas sensor in accordance with claim 12, wherein said powder filler contains at least one of talc and boron nitride by an amount of 50 weight % or more.

18. A gas sensor comprising:
a housing;
a gas sensing element disposed in said housing;
a powder filler stuffed in a filler space defined between said housing and said gas sensing element so as to airtightly seal a clearance between said housing and said gas sensing element, wherein a supplementary filler agent is added to said powder filler;
an outside electrode disposed on a surface of said gas sensing element;
an electrode protecting layer provided on the surface of said gas sensing element so as to cover and protect said outside electrode; and
an uneven surficial layer for enhancing adhesion of said outside electrode to said electrode protecting layer and holding said outside electrode on the surface of said gas sensing element,
wherein proximal ends of said uneven surficial layer and the protecting layer are offset toward a distal end side of said gas sensor with respect to said proximal end of said filler space, and
wherein said outside electrode extends toward a proximal end side of said gas sensor with respect to said proximal end of said filler space.

19. The gas sensor in accordance with claim 18, wherein said supplementary filler agent is inorganic compound which is in a liquid state at 20° C. or a comparable room temperature.

20. The gas sensor in accordance with claim 19, wherein said inorganic compound contains at least one selected from the group consisting of water solution of aluminum primary phosphate, water solution of sodium silicate, and water solution of potassium silicate.

21. The gas sensor in accordance with claim 19, wherein an additive amount of said supplementary filler agent is in a range from 0.1 to 10 weight part with respect to 100 weight part of said powder filler.

22. The gas sensor in accordance with claim 18, wherein said supplementary filler agent is a inorganic compound which is liquefiable at a temperature of 600° C. or less.

23. The gas sensor in accordance with claim 22, wherein said inorganic compound contains at least one selected from the group consisting of barium hydroxide, borosilicate glass, aluminosilicate glass, soda-lime silicate glass, lead silicate glass, low-melting borate glass, lime-alumino group glass, and aluminate glass.

24. The gas sensor in accordance with claim 22, wherein an additive amount of said supplementary filler agent is in a range from 0.5 to 30 weight part with respect to 100 weight part of said powder filler.

25. A gas sensor comprising:
a housing;
a gas sensing element disposed in said housing;
a powder filler stuffed in a filler space defined between said housing and said gas sensing element so as to airtightly seal a clearance between said housing and said gas sensing element;
an outside electrode disposed on a surface of said gas sensing element;
an electrode protecting layer provided on the surface of said gas sensing element so as to cover and protect said outside electrode; and
an uneven surficial layer for enhancing adhesion of said outside electrode to said electrode protecting layer and holding said outside electrode on the surface of said gas sensing element,
wherein proximal ends of said uneven surficial layer and the electrode protecting layer are offset toward a distal end side of said gas sensor with respect to said proximal end of said filler space, and
wherein said outside electrode extends toward a proximal end side of said gas sensor with respect to said proximal end of said filler space.

26. The gas sensor in accordance with claim 25, wherein said at least one of said uneven surficial layer and said electrode protecting layer is offset toward the distal end side of said gas sensor with respect to the proximal end of said filler space by an amount of 0.5 mm or more.

27. The gas sensor in accordance with claim 25, wherein the proximal end of said at least one of said uneven surficial layer and said electrode protecting layer is equal to a distal end of said filler space or offset toward the distal end side of said gas sensor with respect to said distal end of said filler space.

28. A gas sensor comprising:
a housing;
a gas sensing element disposed in said housing;
a powder filler stuffed in a filler space defined between said housing and said gas sensing element so as to airtightly seal a clearance between said housing and said gas sensing element, wherein said powder filler contains grains which are subjected to a classification to remove both of fine and coarse grains before said powder filler is stuffed into said filler space;
an outside electrode disposed on a surface of said gas sensing element;
an electrode protecting layer provided on the surface of said gas sensing element so as to cover and protect said outside electrode; and
an uneven surficial layer for enhancing adhesion of said outside electrode to said electrode protecting layer and holding said outside electrode on the surface of said gas sensing element,
wherein proximal ends of said uneven surficial layer and the electrode protecting layer are offset toward a distal end side of said gas sensor with respect to said proximal end of said filler space, and
wherein said outside electrode extends toward a proximal end side of said gas sensor with respect to said proximal end of said filler space.

29. A gas sensor comprising:
a housing;
a gas sensing element disposed in said housing;
a powder filler stuffed in a filler space defined between said housing and said gas sensing element so as to airtightly seal a clearance between said housing and said gas sensing element, wherein a supplementary filler agent is added to said powder filler, said powder filler contains grains whose diameter is in a range from 80 μm to 5,000 μm when measured before being stuffed into said filler space, and a weight percentage of said grains having the diameter of 80 μm to 5,000 μm is equal to or larger than 80% with respect to an overall weight of said powder filler;
an outside electrode disposed on a surface of said gas sensing element;
an electrode protecting layer provided on the surface of said gas sensing element so as to cover and protect said outside electrode; and
an uneven surficial layer for enhancing adhesion of said outside electrode to said electrode protecting layer and holding said outside electrode on the surface of said gas sensing element,
wherein proximal ends of said uneven surficial layer and the protecting layer are offset toward a distal end side of said gas sensor with respect to said proximal end of said filler space, and
wherein said outside electrode extends toward a proximal end side of said gas sensor with respect to said proximal end of said filler space.

30. A gas sensor comprising:
a housing;
a gas sensing element disposed in said housing;
a powder filler stuffed in a filler space defined between said housing and said gas sensing element so as to airtightly seal a clearance between said housing and said gas sensing element, wherein a supplementary filler agent is added to said powder filler, and said powder filler contains grains which are subjected to a classification to remove both of fine and coarse grains before powder filler is stuffed into said filler space;
an outside electrode disposed on a surface of said gas sensing element;
an electrode protecting layer provided on the surface of said gas sensing element so as to cover and protect said outside electrode; and
an uneven surficial layer for enhancing adhesion of said outside electrode to said electrode protecting layer and holding said outside electrode on the surface of said gas sensing element,
wherein proximal ends of said uneven surficial layer and the protecting layer are offset toward a distal end side of said gas sensor with respect to said proximal end of said filler space, and
wherein said outside electrode extends toward a proximal end side of said gas sensor with respect to said proximal end of said filler space.

31. A gas sensor comprising:
a housing;
a gas sensing element disposed in said housing;
a powder filler stuffed in a filler space defined between said housing and said gas sensing element so as to airtightly seal a clearance between said housing and said gas sensing element, wherein a supplementary filler agent is added to said powder filler, said powder filler contains grains which are subjected to a classification to remove both of fine and coarse grains before said powder filler is stuffed into said filler space;
an electrode protecting layer provided on the surface of said gas sensing element so as to cover and protect said outside electrode; and
an uneven surficial layer for enhancing adhesion of said outside electrode to said electrode protecting layer and holding said outside electrode on the surface of said gas sensing element,
wherein proximal ends of said uneven surficial layer and the electrode protecting layer are offset toward a distal end side of said gas sensor with respect to said proximal end of said filler space, and
wherein said outside electrode extends toward a proximal end side of said gas sensor with respect to said proximal end of said filler space.

* * * * *